(12) United States Patent
Hotta et al.

(10) Patent No.: US 12,426,838 B2
(45) Date of Patent: Sep. 30, 2025

(54) BIOLOGICAL SIGNAL MEASUREMENT DEVICE

(71) Applicant: TDK CORPORATION, Tokyo (JP)

(72) Inventors: Yu Hotta, Tokyo (JP); Tomohiko Shibuya, Tokyo (JP)

(73) Assignee: TDK CORPORATION, Tokyo (JP)

( * ) Notice: Subject to any disclaimer, the term of this patent is extended or adjusted under 35 U.S.C. 154(b) by 91 days.

(21) Appl. No.: 18/508,482

(22) Filed: Nov. 14, 2023

(65) Prior Publication Data
US 2024/0156409 A1 May 16, 2024

(30) Foreign Application Priority Data

Nov. 16, 2022 (JP) .................................. 2022-183460
Oct. 5, 2023 (JP) .................................. 2023-173565

(51) Int. Cl.
A61B 5/00 (2006.01)
A61B 5/242 (2021.01)
A61B 5/318 (2021.01)

(52) U.S. Cl.
CPC .............. *A61B 5/721* (2013.01); *A61B 5/242* (2021.01); *A61B 5/6891* (2013.01); *A61B 5/318* (2021.01); *A61B 2560/0242* (2013.01); *A61B 2562/046* (2013.01)

(58) Field of Classification Search
CPC ....... A61B 5/721; A61B 5/242; A61B 5/6891; A61B 5/318; A61B 2560/0242; A61B 2562/046; A61B 5/05; A61B 2562/0223; A61B 5/11; A61B 5/18; A61B 5/6893; A61B 5/7207

See application file for complete search history.

(56) References Cited

U.S. PATENT DOCUMENTS

| | | | |
|---|---|---|---|
| 11,744,759 B2 * | 9/2023 | Waterson | G01G 19/44 297/188.01 |
| 2004/0222892 A1 * | 11/2004 | Balaban | A61B 5/18 340/576 |
| 2008/0097188 A1 * | 4/2008 | Pool | A61B 17/1355 600/12 |

(Continued)

FOREIGN PATENT DOCUMENTS

WO 2014/192636 A1 12/2014

OTHER PUBLICATIONS

Jan. 17, 2024 Search Report issued in European Patent Application No. 23209444.1.

*Primary Examiner* — Baisakhi Roy
(74) *Attorney, Agent, or Firm* — Oliff PLC

(57) ABSTRACT

Provided is a biological signal measurement device capable of suppressing an influence of noise derived from a body motion of a test subject on a biological signal measurement result. The biological signal measurement device includes a placement portion on which a test subject is placed, one or more measurement sensors configured to measure a biological signal regarding the test subject, and a sensor holder configured to hold the measurement sensors. The placement portion has a recess. At least a part of the measurement sensor is arranged inside of the recess of the placement portion. The sensor holder and the measurement sensors are arranged to be physically separated from the placement portion without coming into contact with the placement portion.

10 Claims, 23 Drawing Sheets

(56) References Cited

U.S. PATENT DOCUMENTS

| | | | |
|---|---|---|---|
| 2009/0295385 A1* | 12/2009 | Brazdeikis | A61B 5/242 |
| | | | 324/309 |
| 2016/0220163 A1* | 8/2016 | Yamada | G16H 20/70 |
| 2018/0079321 A1* | 3/2018 | Sugiyama | B60N 2/70 |
| 2018/0118071 A1* | 5/2018 | Sugiyama | A47C 7/744 |
| 2019/0167135 A1* | 6/2019 | Okada | A61B 5/242 |
| 2020/0109985 A1* | 4/2020 | Young | A47C 19/027 |
| 2022/0364905 A1* | 11/2022 | Young | G08B 21/22 |
| 2024/0083317 A1* | 3/2024 | Sugiyama | A47C 9/02 |

\* cited by examiner

BIOLOGICAL SIGNAL MEASUREMENT DEVICE

CROSS-REFERENCE TO RELATED APPLICATION

Priority is claimed on Japanese Patent Application No. 2022-183460, filed Nov. 16, 2022 and Japanese Patent Application No. 2023-173565, filed Oct. 5, 2023, the content of which is incorporated herein by reference.

BACKGROUND OF THE INVENTION

Field of the Invention

The present disclosure relates to a biological signal measurement device.

DESCRIPTION OF RELATED ART

For example, in a chair-type biological signal measurement device, a sensor for measuring a biological signal (a measurement sensor) may be provided inside of a chair and noise derived from a body motion of a subject may be superimposed on a measurement result. Here, the body motion includes, for example, breathing or the heart beating.

Although there is a frequency filtering method using a high-pass filter or a low-pass filter as a representative noise cancellation method of cancelling such noise, the body motion noise also affects a signal of interest when a frequency band of the signal (the signal of interest) desired to be measured is close to a frequency band of the body motion noise.

For example, in a biological information detection device for a vehicle seat described in Patent Document 1, a plurality of biological sensors are distributed and provided inside of the seat (see Patent Document 1).

PATENT DOCUMENTS

[Patent Document 1] PCT International Publication No. WO2014/192636

SUMMARY OF THE INVENTION

However, in the conventional technology, because a biological sensor (a measurement sensor) is embedded in a seat, an influence of noise derived from a body motion of a subject superimposed on a measurement result is large.

As a specific example, when a magnetic sensor is used as a measurement sensor, because the magnetic sensor is easily affected by vibration, the influence of noise derived from the body motion of the subject is large. In particular, when the subject's body directly comes into contact with the magnetic sensor or when the magnetic sensor comes into contact with the seat with which the subject's body is in contact, the influence of such noise is large.

The present disclosure has been made in consideration of such circumstances and an objective of the present disclosure is to provide a biological signal measurement device capable of suppressing an influence of noise derived from a body motion of a test subject on a biological signal measurement result.

According to an aspect of the present disclosure, there is provided a biological signal measurement device including: a placement portion on which a test subject is placed; one or more measurement sensors configured to measure a biological signal regarding the test subject; and a sensor holder configured to hold the measurement sensors, wherein the placement portion has a recess, wherein at least a part of the measurement sensor is arranged inside of the recess of the placement portion, and wherein the sensor holder and the measurement sensors are arranged to be physically separated from the placement portion without coming into contact with the placement portion.

A biological signal measurement device according to the present disclosure can suppress an influence of noise derived from a body motion of a test subject on a biological signal measurement result.

DETAILED DESCRIPTION OF THE INVENTION

Hereinafter, embodiments of the present disclosure will be described with reference to the drawings.

Although each component constituting the device is given a name for convenience of description, other names may be used. Also, each component is not necessarily limited to the illustrated configuration and other configurations may be used.

First Embodiment

[Biological Signal Measurement Device]

Figure 1:
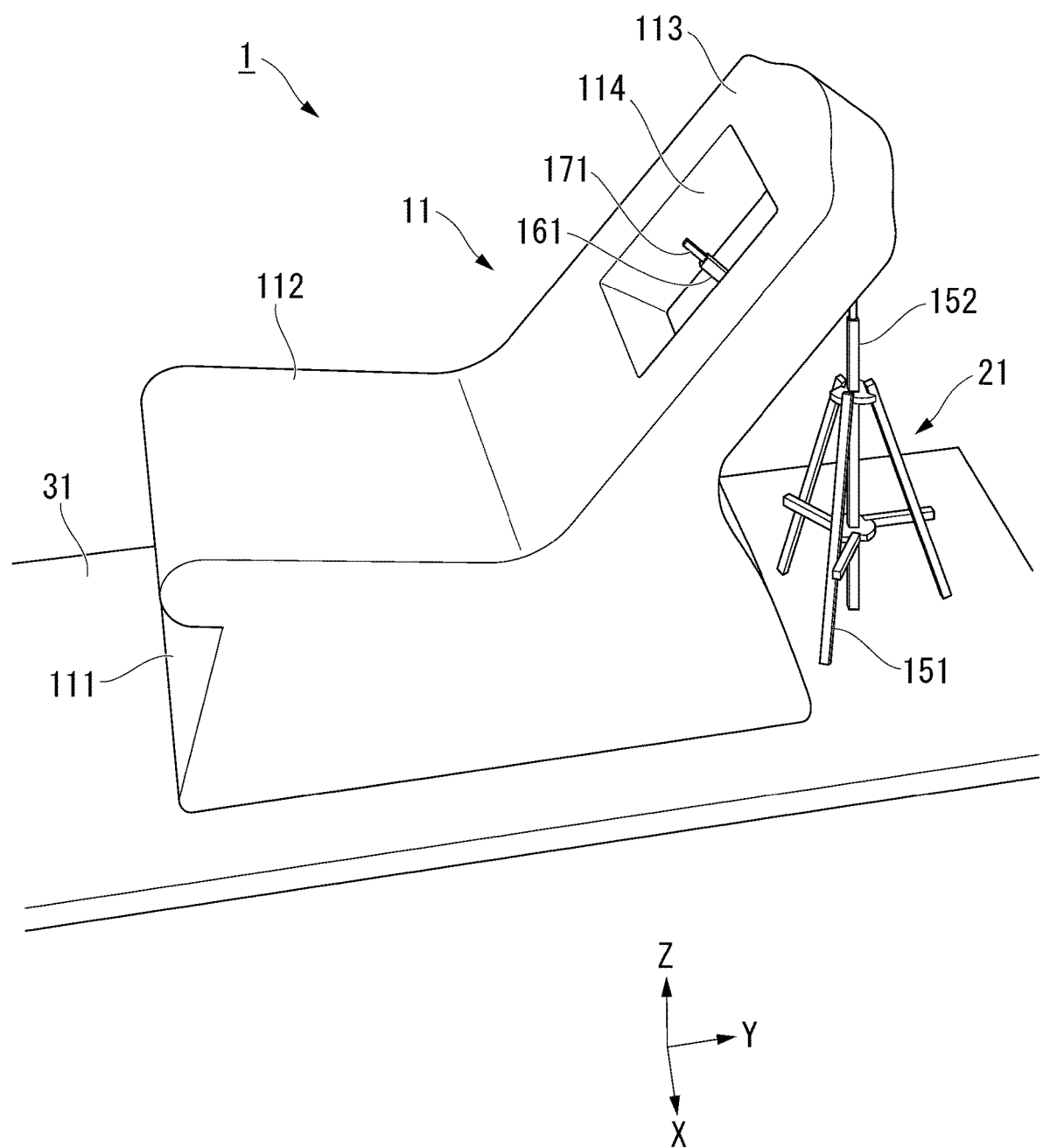
FIG. 1 is a diagram showing an example of a configuration of a biological signal measurement device according to an embodiment (a first embodiment).

FIG. 1 is a diagram showing an example of a configuration of a biological signal measurement device 1 according to an embodiment (a first embodiment).

Figure 2:
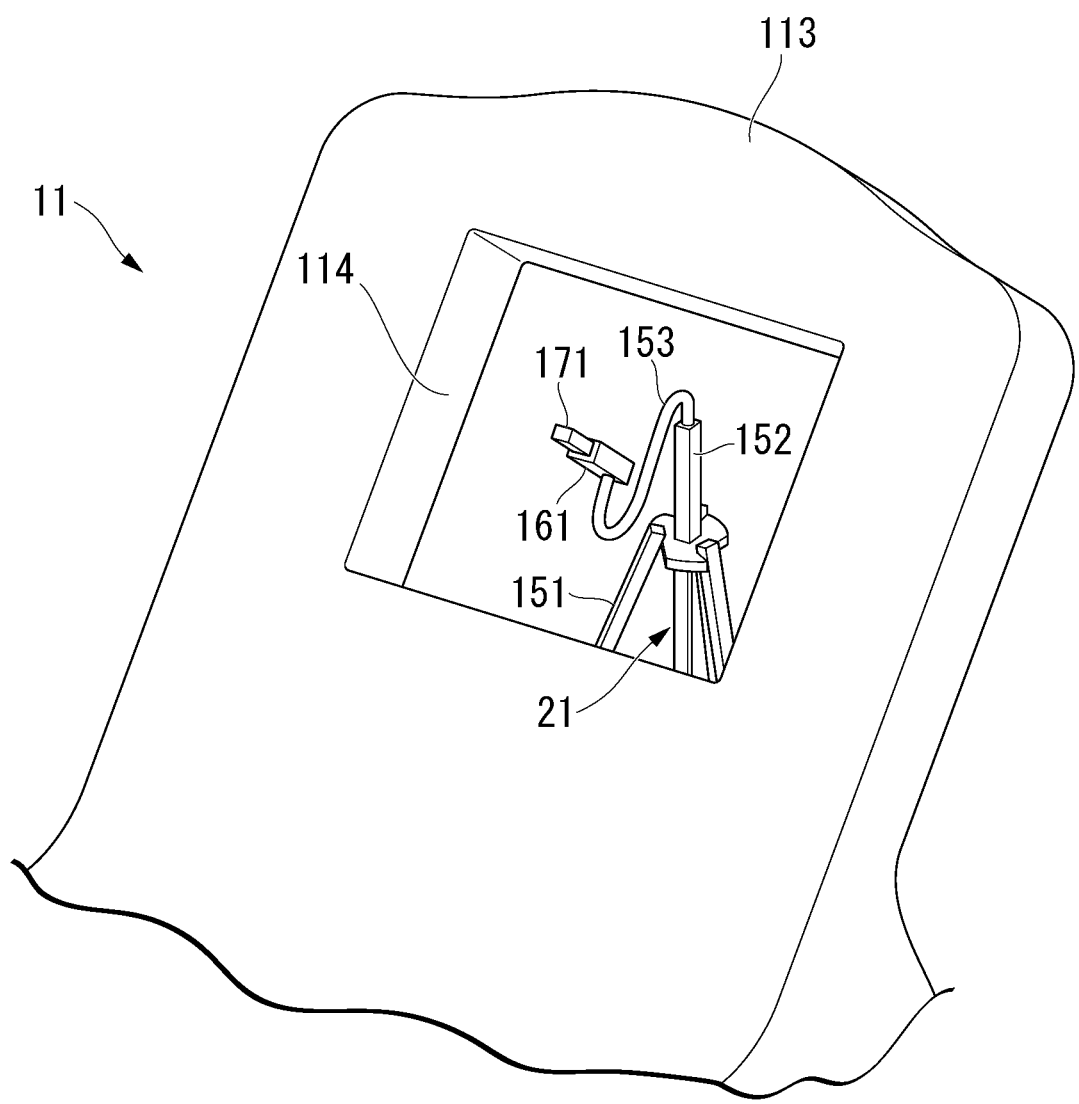
FIG. 2 is a diagram showing an example of a configuration near a recess of the biological signal measurement device according to the embodiment (the first embodiment).

FIG. 2 is a diagram showing an example of a configuration near a recess 114 of the biological signal measurement device 1 according to the embodiment (the first embodiment).

For convenience of description, an XYZ Cartesian coordinate system, which is a three-dimensional Cartesian coordinate system, is shown in FIGS. 1 and 2.

In the present embodiment, a direction parallel to a Z-axis is a direction parallel to a gravity direction. A positive side of the Z-axis is an upper side and a negative side of the Z-axis is a lower side.

Also, in the present embodiment, an XY-plane is a plane perpendicular to the gravity direction.

The biological signal measurement device 1 includes a chair 11, a sensor holder 21, and a measurement sensor 171.

In the present embodiment, a state in which the chair 11 and the sensor holder 21 constituting the biological signal measurement device 1 are placed directly or indirectly (for example, via an anti-vibration portion) on an installation portion will be described as an example.

The installation portion is a place where the biological signal measurement device 1 is placed, and is, for example, a floor surface, a board surface, or the like.

In the example of FIG. 1, an installation surface is a surface of a board 31.

The board 31 may be configured using, for example, a cushioning material, and can absorb vibration (shock) with the cushioning material to reduce noise included in a measurement result of the measurement sensor 171.

Here, in the present embodiment, the surface of the board 31 is assumed to be a surface (a horizontal surface) perpendicular to the gravity direction (a vertical direction).

In addition, the biological signal measurement device 1 may be installed on a surface in another orientation, and may be installed, for example, on a surface slightly inclined from the horizontal direction.

In the present embodiment, a case where a living body serving as a biological signal measurement target is a human is shown. In the present embodiment, the human may be referred to as a subject.

As another example, the living body may be an animal other than a human.

In the present embodiment, a case where a magnetic signal issued from a living body is measured as a biological signal is shown.

As another example, the biological signal may be an electrical signal issued from the living body or a temperature signal issued from the living body. As a specific example, the biological signal may be an electrocardiogram signal.

<Chair>

The chair 11 is an example of a placement portion on which a test subject (a subject in the present embodiment) is placed.

The chair 11 includes a leg portion 111, a seat surface portion 112, and a backrest portion 113.

The leg portion 111 is a base portion and has a bottom surface. The bottom surface is in contact with the installation surface (the surface of the board 31 in the example of FIG. 1). In the present embodiment, the bottom surface is a flat surface (or a substantially flat surface).

The seat surface portion 112 is provided above the leg portion 111.

Here, the seat surface portion 112, for example, may be configured integrally with the leg portion 111, or may be configured separately from the leg portion 111.

The seat surface portion 112 has a seat surface in an upward direction. The seat surface may be, for example, a surface parallel to the horizontal plane or a surface having an inclination with respect to the horizontal plane.

The backrest portion 113 is provided above the leg portion 111.

Here, the backrest portion 113 may be configured integrally with, for example, at least one of the leg portion 111 and the seat surface portion 112, or may be configured separately therefrom.

The backrest portion 113 extends at a predetermined angle in a diagonally upward direction with respect to the seat surface of the seat surface portion 112.

Here, an angle between the seat surface of the seat surface portion 112 and the back surface of the backrest portion 113 is less than 180 degrees.

The backrest portion 113 has a recess 114.

In the present embodiment, the recess 114 is a hole portion (a through-hole portion) that penetrates the upper surface and the lower surface of the backrest portion 113. The recess 114 is provided in a region of a part of the surfaces (upper and lower surfaces) of the backrest portion 113. That is, the recess 114 has a structure in which a part of the backrest portion 113 of the chair 11 is hollowed out. Although an example in which the recess 114 is penetrated is shown in the present embodiment, a non-penetrating recess may be used as another example. For example, a recess having a structure that seems to be partially hollowed out without being penetrated from the lower surface of the backrest portion 113 may be used.

Here, in the present embodiment, the recess 114 has a square (or substantially square) shape on the surfaces (upper and lower surfaces) of the backrest portion 113, but other shapes may be used. For example, a shape of a rectangle, a circle, an ellipse, or the like may be used.

<Sensor Holder>

The sensor holder 21 includes a tripod portion 151, a shaft portion 152, and a connection portion 153.

The tripod portion 151 is a base portion and is in contact with the installation surface (the surface of the board 31 in the example of FIG. 1).

The shaft portion 152 is a rod-shaped portion. One end of the shaft portion 152 is connected to the tripod portion 151 and the other end of the shaft portion 152 is connected to one end of the connection portion 153.

The connection portion 153 has a predetermined linear shape in the present embodiment.

One end of the connection portion 153 is connected to the other end of the shaft portion 152. The other end of the connection portion 153 has an attachment portion 161 to which the measurement sensor 171 can be attached.

The attachment portion 161 has a mechanism that enables the measurement sensor 171 to be attached and detached.

In the examples of FIGS. 1 and 2, the measurement sensor 171 is attached to the attachment portion 161.

Here, the tripod portion 151, the shaft portion 152, and the connection portion 153 may have, for example, a configuration in which they can be attached to and detached from each other, or some or all may be integrated.

Also, the attachment portion 161 and the measurement sensor 171 may be integrated (fixedly) so that detachment is impossible as another example.

<Measurement Sensor>

The measurement sensor 171 has a function of measuring a biological signal related to a test subject (a subject in the present embodiment). In the present embodiment, the measurement sensor 171 is a magnetic sensor that measures a magnetic signal issued from a living body.

Although a predetermined surface of the measurement sensor 171 is connected to the attachment portion 161 in the present embodiment, other forms may be used as an attachment form. The measurement sensor 171 detects, for example, a detection target (for example, magnetism or the like) at a sensitivity point inside the sensor.

<Arrangement of Chair and Sensor Holder>

In the present embodiment, the chair 11 and the sensor holder 21 (and the measurement sensor 171) are physically separate and completely independent.

Also, the chair 11 and the sensor holder 21 (and the measurement sensor 171) are arranged without coming into contact with each other.

In the example of FIG. 1, the sensor holder 21 is installed below the lower surface of the backrest portion 113 of the chair 11 (or in the vicinity thereof).

Also, the measurement sensor 171 is inserted into the recess 114 from the lower surface side of the backrest portion 113 of the chair 11. The measurement sensor 171 is arranged at a position that does not reach a surface parallel (or substantially parallel) to the upper surface of the backrest portion 113.

<Usage State of Biological Signal Measurement Device>

Figure 3:
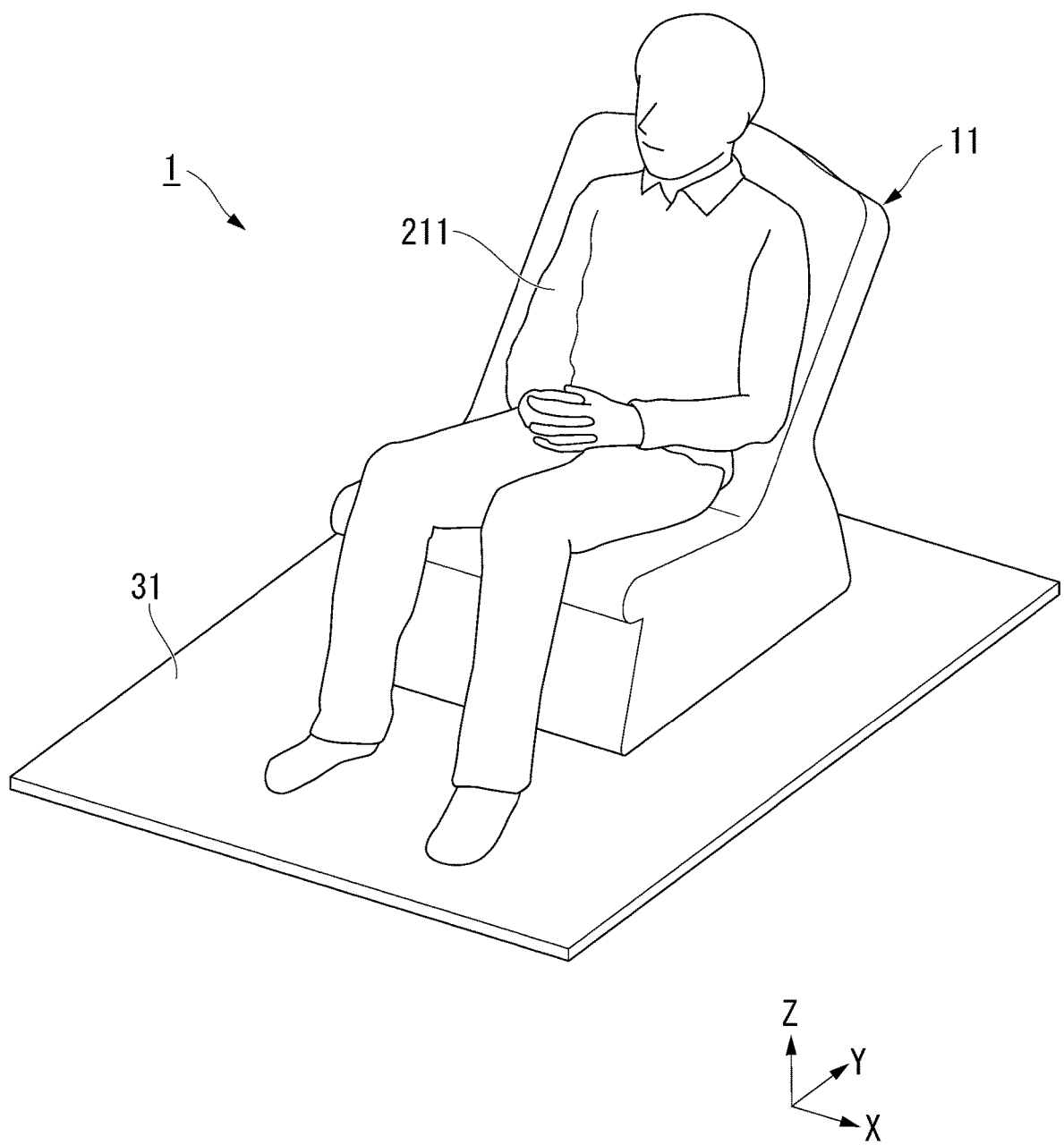
FIG. 3 is a diagram showing an example of a usage state of the biological signal measurement device according to the embodiment (the first embodiment).

FIG. 3 is a diagram showing an example of a usage state of the biological signal measurement device 1 according to the embodiment (the first embodiment).

FIG. 3 shows the same XYZ Cartesian coordinate system as FIG. 1.

In the example of FIG. 3, a state in which a human subject 211 is sitting in the chair 11 is shown.

The subject 211 sits in the seat surface portion 112 of the chair 11 and the back of the subject 211 comes into contact with the upper surface of the backrest portion 113. The feet of the subject 211 are in contact with the surface of the board 31.

In the example of FIG. 3, the recess 114 of the backrest portion 113 is included in a back surface of the subject 211.

In the usage state as shown in FIG. 3, the sensor holder 21 and the measurement sensor 171 are arranged at a position where they do not come into contact with the chair 11 and the subject 211.

Although the measurement sensor 171 can measure a magnetic signal caused by the heart of the subject 211 in the example of FIG. 3, it is not limited thereto. A configuration in which other biological signals are measured may be used.

As described above, in the biological signal measurement device 1 according to the present embodiment, it is possible to suppress the influence of noise derived from the body motion of the test subject (the subject 211 in the present embodiment) on the biological signal measurement result.

In the biological signal measurement device 1 according to the present embodiment, it is possible to suppress the influence of noise derived from the body motion of the subject 211 superimposed on the measurement result of the measurement sensor 171 by making an arrangement in which the sensor holder 21 and the measurement sensor 171 do not come into contact with the subject 211 in a state in which the subject 211 is sitting in the chair 11.

Here, in the biological signal measurement device 1 according to the present embodiment, the recess 114 is provided on the back surface of the chair 11 and at least a part (or all) of the measurement sensor 171 is arranged inside of the recess 114. Also, when the biological signal is measured (when the state is the used state), the sensor holder 21, the measurement sensor 171, and the chair 11 have a completely physically separate structure and are arranged so that they do not come into contact with each other.

With such an arrangement, a configuration in which the body motion of the subject 211 is not transmitted to the measurement sensor 171 is implemented and the noise derived from the body motion (body motion noise) is prevented from being superimposed on the measurement result.

Also, it is possible to make the measurement sensor 171 close to the body of the subject 211 by arranging at least a part of the measurement sensor 171 inside of the recess 114.

Thus, in the biological signal measurement device 1 according to the present embodiment, for example, it is possible to shorten a distance between the subject 211 and the measurement sensor 171 while preventing noise derived from the body motion of the subject 211 from being superimposed on the measurement result of the measurement sensor 171.

Also, in the biological signal measurement device 1 according to the present embodiment, for example, the position of the measurement sensor 171 can be arranged at an appropriate position in accordance with the physique of the subject 211 or a signal of interest thereof.

Here, the signal of interest is a signal (a biological signal) desired to be measured and may be referred to as a target signal or the like.

Here, for example, as in the technology described in Patent Document 1, when a measurement sensor is provided inside of a chair, it is often difficult to change the arrangement of the measurement sensor according to the physique of the subject or the like.

On the other hand, in the biological signal measurement device 1 according to the present embodiment, for example, measurement can be performed without contact between the measurement sensor 171 and the subject 211 and a positional relationship between the subject 211 and the measurement sensor 171 can be appropriately adjusted.

Here, a case where one sensor holder 21 is used has been described in the present embodiment, but the number of sensor holders may be two or more.

Although a case where one measurement sensor 171 is attached to one sensor holder 21 has been described in the present embodiment, a configuration in which two or more measurement sensors are attached to one sensor holder may be used as another example.

Also, various arrangements may be used as the arrangement of the sensor holder 21 and the arrangement of the measurement sensor 171.

Also, the shape of the recess 114 of the chair 11 may be any shape, and, for example, the recess may be circular or elliptical on the surfaces (upper and lower surfaces) of the backrest portion 113 of the chair 11.

Also, any position may be used as the position where the recess is formed in the chair 11 and, for example, a position corresponding to a part of the body of the subject 211 sitting in the chair 11 may be used.

Also, the number of recesses provided in the chair 11 is not necessarily limited to one and two or more recesses may be provided.

<Material of Chair>

In the biological signal measurement device 1 according to the present embodiment, for example, the material of the chair 11 may be made of a non-magnetic body instead of a magnetic body.

In such a configuration, for example, magnetic noise caused by vibration of the magnetic body in the chair can be eliminated and therefore the influence of noise derived from the body motion of the subject 211 to be superimposed on the measurement result of the measurement sensor 171 (a magnetic signal in the present embodiment) can be reduced and the accuracy of the measurement result of the measurement sensor 171 (the magnetic signal in the present embodiment) can be improved.

Here, as the non-magnetic body, for example, a non-magnetic metal, wood, leather, or a resin such as urethane or acrylic may be used.

For example, the inside of the chair 11 may be packed with a resin such as urethane.

As another example, the material of the chair 11 may include a magnetic body.

[Example of Configuration with Adjustable Arrangement of Measurement Sensor]

In the biological signal measurement device 1 shown in FIGS. 1 and 2, the connection portion 153 of the sensor holder 21 may be further configured as a deformable member. The member is not particularly limited, and may be, for example, a flexible arm. The flexible arm may be made of, for example, a deformable resin or metal.

In the present example, the arrangement of the measurement sensor 171 can be adjusted (changed) by deforming the connection portion 153 according to a manual operation of an operator of the biological signal measurement device 1 or the like.

Here, for example, one or both of an adjustment of a position of the measurement sensor 171 and an adjustment of an angle of the measurement sensor 171 (for example, an angle at which a predetermined surface or the like is directed) are included as an adjustment of the arrangement of the measurement sensor 171.

As described above, in the biological signal measurement device 1 according to the present example, the arrangement of the measurement sensor 171 can be adjusted. Thereby, for example, the subject 211 can be measured in a comfortable posture and a biological signal can be measured in a stable state.

In the biological signal measurement device 1 according to the present example, the measurement sensor 171 can be freely arranged inside of the recess 114 of the chair 11 or the like and a position or an angle of the measurement sensor 171 can be adjusted in accordance with a physique of the subject 211 or a position of a measurement site (for example, a body part such as the heart) of the biological signal.

Here, the configuration in which the arrangement of the measurement sensor 171 can be adjusted is not limited to the present example, and any other configuration may be used.

Although a configuration in which the arrangement of the measurement sensor 171 can be adjusted manually by an operator or the like is shown in the present example, a configuration in which the arrangement of the measurement sensor 171 can be adjusted by an electric device (for example, a motor or the like) may be used as another example. In this case, the biological signal measurement device 1 may include an operation portion operated by an operator or the like to issue an instruction to change the arrangement of the measurement sensor 171 (for example, one or both of the position and the angle thereof).

Second Embodiment

[Biological Signal Measurement Device]

Figure 4:
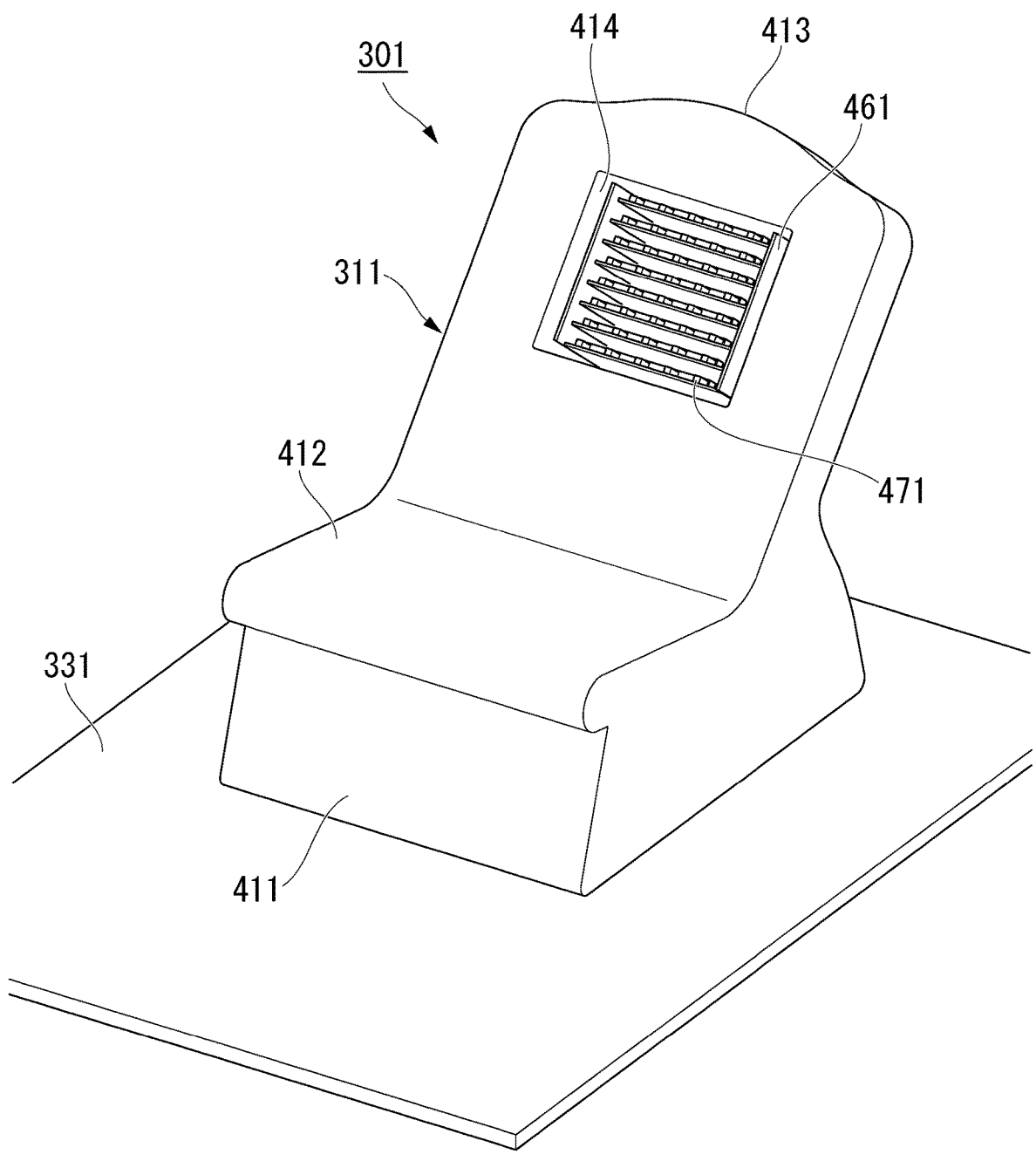
FIG. 4 is a diagram showing an example of a configuration of a biological signal measurement device according to an embodiment (a second embodiment).

FIG. 4 is a diagram showing an example of a configuration of a biological signal measurement device 301 according to an embodiment (a second embodiment).

Figure 5:
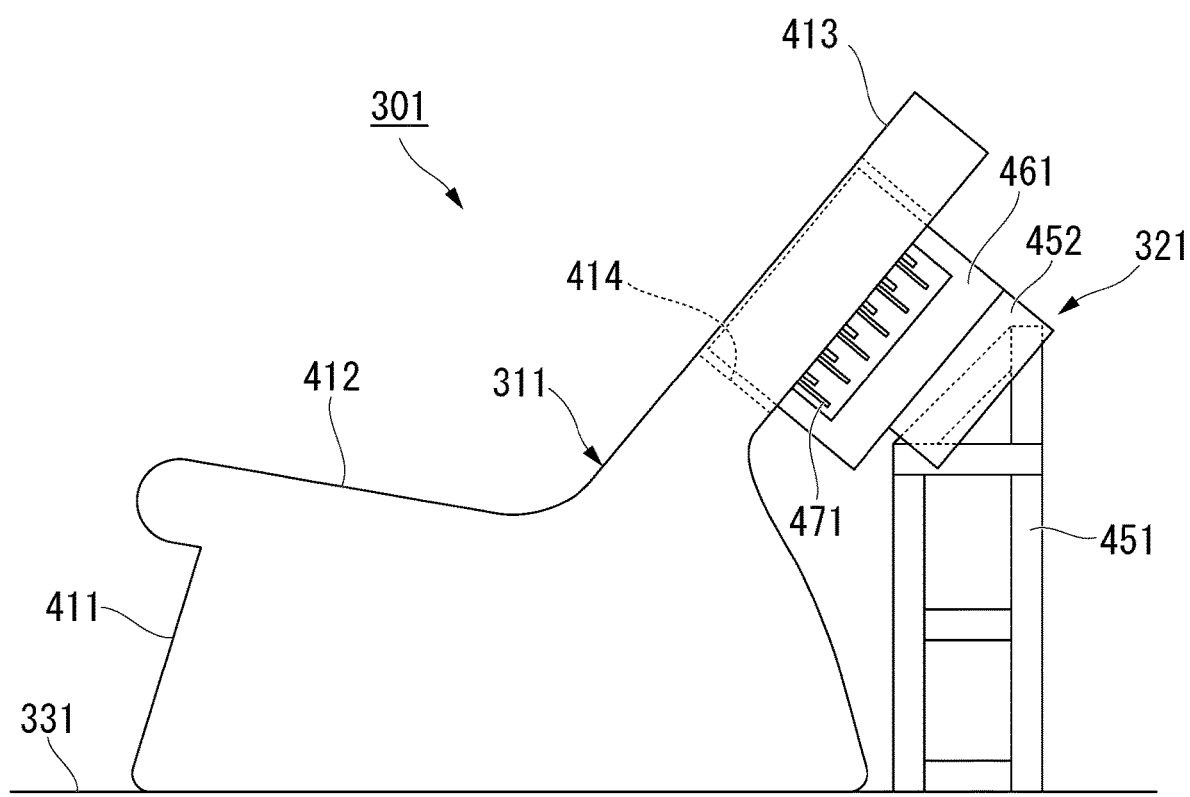
FIG. 5 is a diagram showing an example of a state in which the biological signal measurement device according to the embodiment (the second embodiment) is viewed from a side surface.

FIG. 5 is a diagram showing an example of a state in which the biological signal measurement device 301 according to the embodiment (the second embodiment) is viewed from a side surface. In the example of FIG. 5, a state of the side surface from the viewpoint of viewing the negative side of the X-axis from the positive side thereof is shown.

Figure 6:
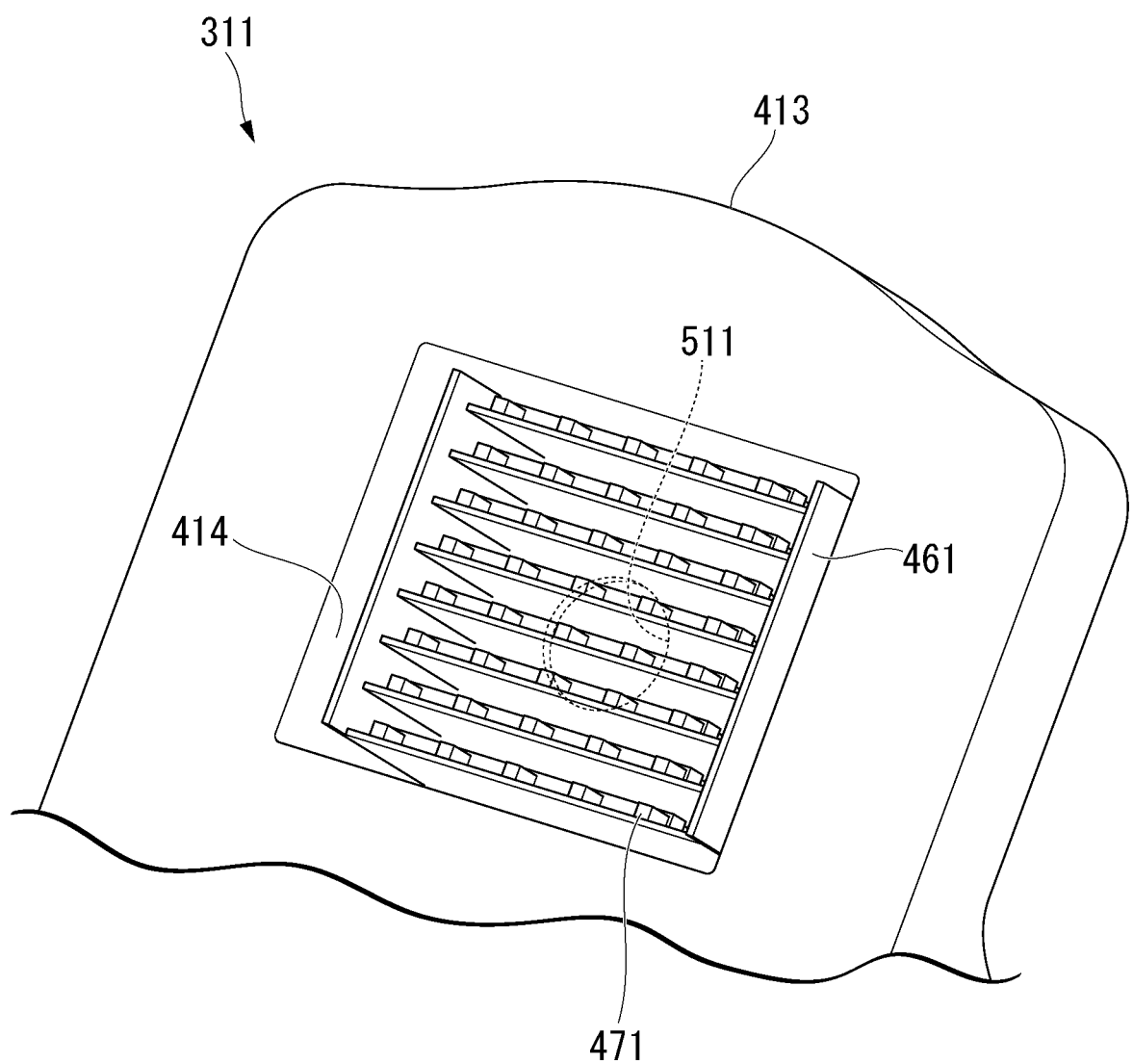
FIG. 6 is a diagram showing an example of a configuration near a recess of the biological signal measurement device according to the embodiment (the second embodiment).

FIG. 6 is a diagram showing an example of a configuration near a recess 414 of the biological signal measurement device 301 according to the embodiment (the second embodiment).

FIGS. 4, 5, and 6 each show an XYZ Cartesian coordinate system, which is a three-dimensional Cartesian coordinate system, for convenience of description.

In the present embodiment, a direction parallel to a Z-axis is a direction parallel to a gravity direction. A positive side of the Z-axis is an upper side and a negative side of the Z-axis is a lower side.

Also, in the present embodiment, an XY-plane is a plane perpendicular to the gravity direction.

Here, the configuration of the biological signal measurement device 301 according to the present embodiment is schematically different from that of the first embodiment (the example of FIG. 1) in the components related to the sensor holder 321 and the measurement sensor 471, and the other components are similar to those of the first embodiment (the example of FIG. 1)

In the present embodiment, the components different from those in the first embodiment will be described in detail, and detailed description of the components similar to those in the first embodiment will be omitted.

The biological signal measurement device 301 includes a chair 311, a sensor holder 321, and a measurement sensor 471.

In the present embodiment, a state in which the chair 311 and the sensor holder 321 constituting the biological signal measurement device 301 are placed directly or indirectly (for example, via an anti-vibration portion) on an installation portion will be described as an example.

The installation portion is a location where the biological signal measurement device 301 is placed, and is, for example, a floor surface, a board surface, or the like.

In the example of FIG. 4, the installation surface is the surface of a board 331.

The board 331 may be configured using, for example, a cushioning material, and can absorb vibration (shock) with the cushioning material to reduce noise included in a measurement result of the measurement sensor 171.

<Chair>

The chair 311 includes a leg portion 411, a seat surface portion 412, and a backrest portion 413.

The backrest portion 413 has a recess 414.

Here, a configuration of the chair 311 according to the present embodiment is similar to the configuration of the chair 11 according to the first embodiment (the example of FIG. 1) and detailed description thereof will be omitted.

<Sensor Holder>

The sensor holder 321 includes a base portion 451, a support portion 452, and a sensor housing portion 461.

Here, two support portions 452 are provided with respect to the base portion 451 in the present embodiment, but one support portion 452 is denoted by a reference sign for convenience of description. These two support portions 452 are provided on one side (the positive side of the X-axis) and the other side (the negative side of the X-axis) in a width direction (for example, a direction parallel to the X-axis).

The base portion 451 is a base portion and is in contact with an installation surface (the surface of the board 331 in the example of FIG. 4).

In the present embodiment, the base portion 451 is configured by combining a plurality of plate-shaped members, but is not limited thereto. Any configuration may be used.

The support portion 452 is a portion in which the upper surface is plate-shaped. The support portion 452 is connected to the upper part of the base portion 451 and the upper surface of the support portion 452 is connected to the back surface of the sensor housing portion 461.

In the present embodiment, the upper surface of the support portion 452 is arranged so that a height position of one side of the pair of sides is above a height position of the other side in the horizontal direction. That is, in the side view, the upper surface of the support portion 452 is oblique in the upward/downward direction.

In the present embodiment, for example, an attachment portion to which the sensor housing portion 461 can be attached is provided on the upper surface side of the support portion 452.

In the present embodiment, the attachment portion has a mechanism in which the sensor housing portion 461 can be attached and detached.

Here, the base portion 451 and the support portion 452 may have a configuration in which they can be attached to and detached from each other, for example, or they may be integrated.

Also, the support portion 452 and the sensor housing portion 461 may be integrated so that detachment is impossible.

The sensor housing portion 461 is a housing portion capable of housing measurement sensors and is a housing portion capable of housing a plurality of measurement sensors in an array shape in the present embodiment.

In the present embodiment, the sensor housing portion 461 schematically has a cuboid shape, one surface of the cuboid is open, and a mechanism (housing mechanism) for housing a plurality of measurement sensors in an array shape is provided in an inner portion (a hollow portion) passing through an opening. In the present embodiment, the array of the plurality of measurement sensors is an array in which a plurality of measurement sensors are arranged in parallel to one of orthogonal sides of the opening surface of the sensor housing portion 461 and in parallel to the other side, and is, for example, an array in which measurement sensors are regularly arranged in a grid shape. In addition, a plurality of sensors (here, measurement sensors) arranged in an array in this way may be referred to as a sensor array.

Although the sensor housing portion 461 having a structure capable of housing a plurality of measurement sensors in an array shape is shown in the present embodiment, the present disclosure is not limited thereto. A sensor housing portion having a structure that can house measurement sensors in any other arrangement may be used.

Here, the housing mechanism of the sensor housing portion 461 is a mechanism in which each of the plurality of measurement sensors can be attached and detached, but the housing mechanism of the sensor housing portion 461 and the measurement sensor may be fixedly integrated as another example.

In an example of FIG. 4 or the like, the surface (the back surface) facing the opening surface of the sensor housing portion 461 is attached to the upper surface of the support portion 452. Thereby, in the side view, the opening surface of the sensor housing portion 461 and the surface (the back surface) facing it are oblique in the upward/downward direction.

In the present embodiment, the surface (the back surface) of the sensor housing portion 461 has a hole portion 511 at a center (or substantially center) position thereof.

Although the hole portion 511 has a circular shape in the present embodiment, it may have other shapes and may have, for example, a shape such as a rectangular shape or an elliptical shape.

Although the hole portion 511 is provided at a center (or substantially center) position thereof on the surface (the back surface) of the sensor housing portion 461 in the present embodiment, the present disclosure is not limited thereto. The hole portion 511 may be provided at other positions.

<Measurement Sensor>

In the present embodiment, a plurality of measurement sensors are attached in an array shape to the housing portion of the sensor housing portion 461.

In the present embodiment, only one measurement sensor 471 of the plurality of measurement sensors is denoted by a reference sign in the example of FIG. 5 or the like.

The measurement sensor 471 has a function of measuring a biological signal related to a test subject (a subject in the present embodiment). In the present embodiment, the measurement sensor 471 is a magnetic sensor that measures a magnetic signal issued from a living body.

Although a predetermined surface of the measurement sensor 471 is arranged to face the outside of the opening of the sensor housing portion 461 in the present embodiment, other forms may be used as the arrangement form.

Here, a case where the sensor housing portion 461 is included in the sensor holder 321 has been described in the present embodiment, but a case where the sensor housing portion 461 is separated from the sensor holder 321 and attached to the sensor holder 321 may be conceived as another example.

<Arrangement of Chair and Sensor Holder>

In the present embodiment, the chair 311 and the sensor holder 321 (and the plurality of measurement sensors 471) are physically separate and completely independent.

Also, the chair 311 and the sensor holder 321 (and the plurality of measurement sensors 471) are arranged so that they do not come into contact with each other.

In the present embodiment, the sensor housing portion 461 is housed inside of the recess 414 of the chair 311. In addition, the recess 414 of the chair 311 and the sensor housing portion 461 are arranged so that they do not come into contact with each other.

In an example of FIG. 4 or the like, on the surface of the opening of the sensor housing portion 461, the lower side of the surface between a pair of upper and lower sides of the surface is arranged to be located below the backrest portion 413 (below the recess 414) and the upper side of the surface is arranged to be located above the backrest portion 413 (above the recess 414).

<Usage State of Biological Signal Measurement Device>

The usage state of the biological signal measurement device 301 is similar to that in the example of FIG. 3.

<Example of State of Back Surface of Biological Signal Measurement Device>

Figure 7:
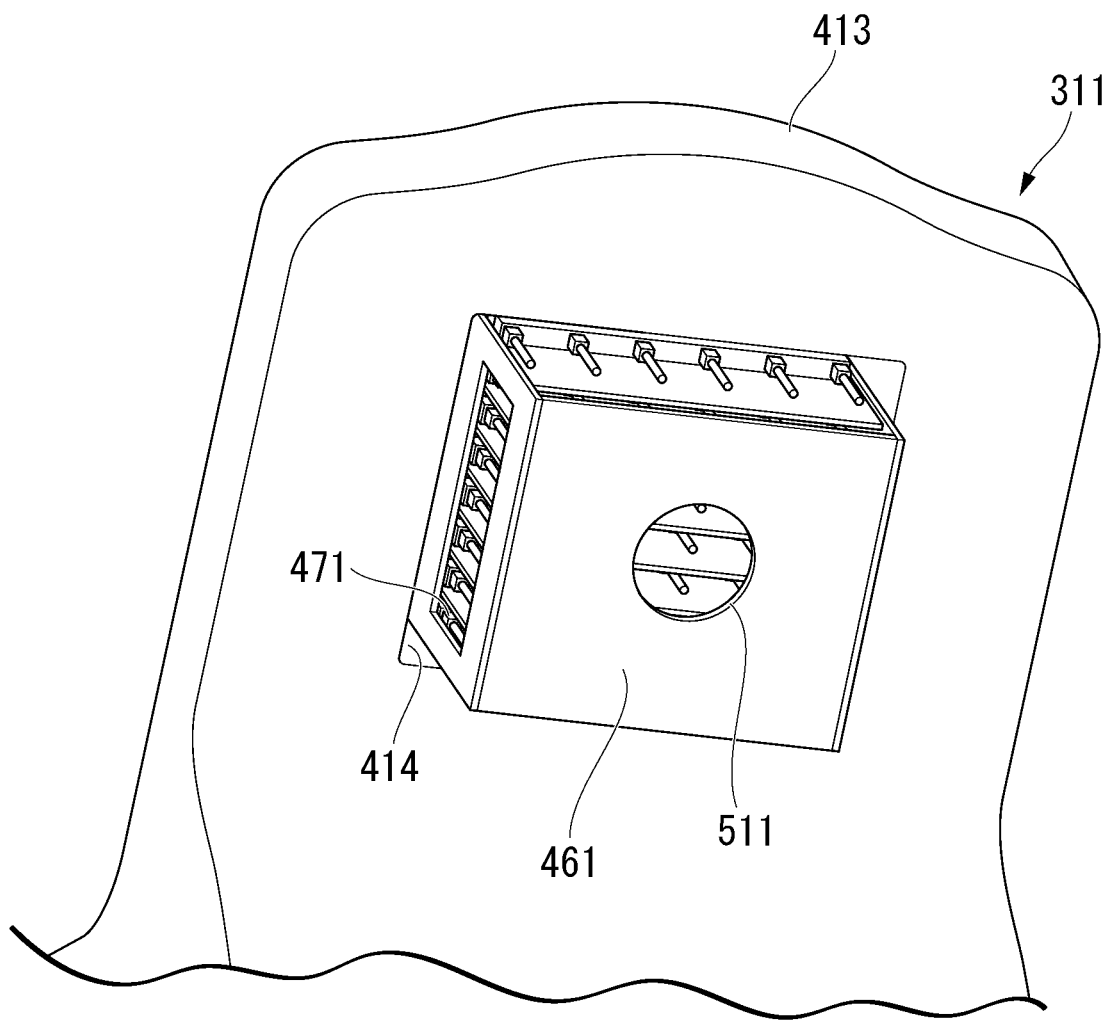
FIG. 7 is a diagram showing an example of a state in which a region near the recess of the biological signal measurement device other than a base portion and a plate-shaped portion is viewed from below a back surface according to the embodiment (the second embodiment).

FIG. 7 is a diagram showing an example of a state in which a region near the recess 414 of the biological signal measurement device 301 other than the base portion 451 and the support portion 452 is viewed from below the back surface according to the embodiment (the second embodiment).

Figure 8:
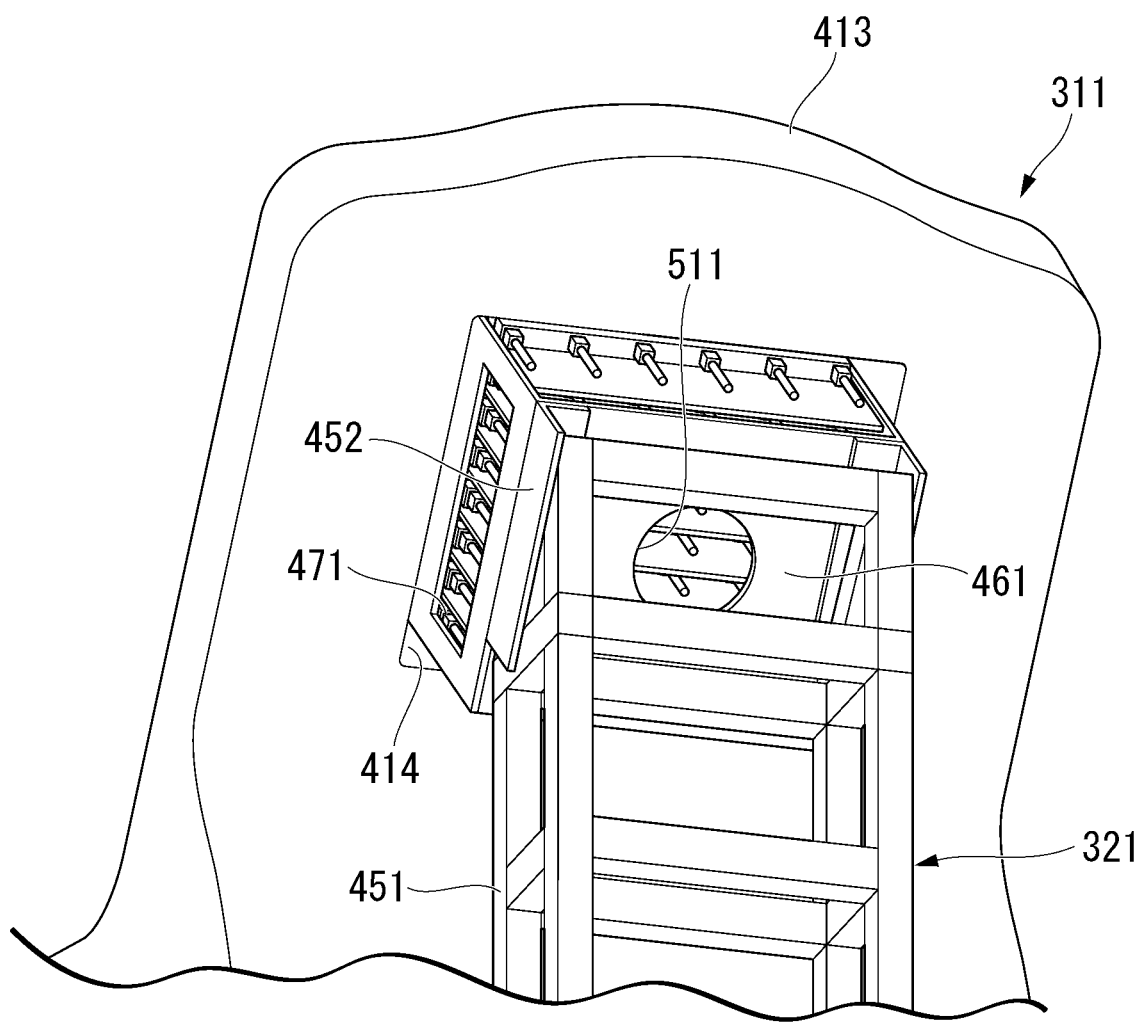
FIG. 8 is a diagram showing an example of a state in which a region near the recess of the biological signal measurement device according to the embodiment (the second embodiment) is viewed from below the back surface.

FIG. 8 is a diagram showing an example of a state in which a region near the recess 414 of the biological signal measurement device 301 according to the embodiment (the second embodiment) is viewed from below the back surface.

Figure 9:
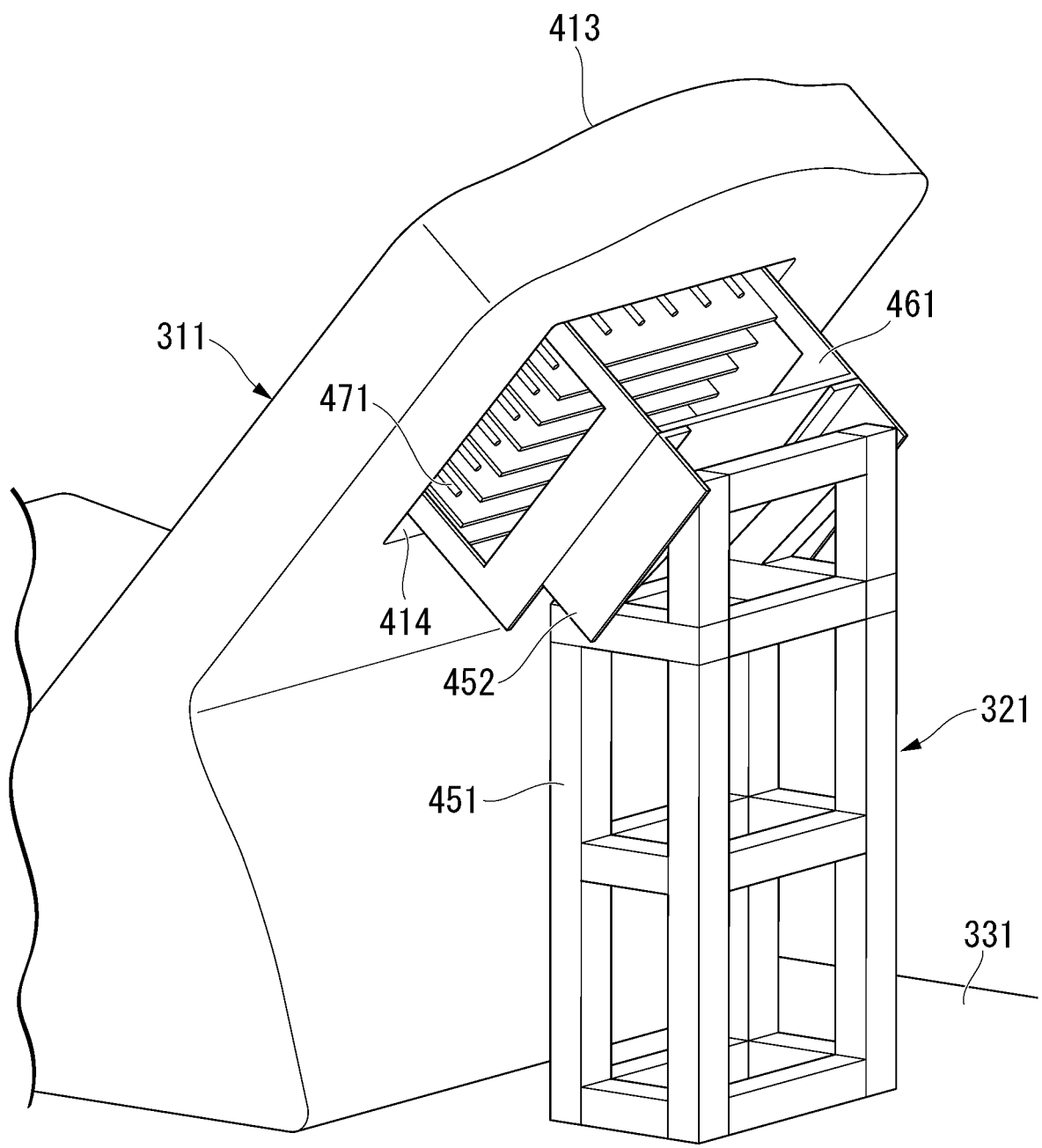
FIG. 9 is a diagram showing an example of a state in which the biological signal measurement device according to the embodiment (the second embodiment) is viewed from below the back surface.

FIG. 9 is a diagram showing an example of a state in which the biological signal measurement device 301 according to the embodiment (the second embodiment) is viewed from below the back surface.

FIGS. 7, 8, and 9 each show an XYZ Cartesian coordinate system similar to that of FIG. 4.

<Hole Portion of Sensor Housing Portion>

In the present embodiment, each measurement sensor 471 is connected to one end of a cable (not shown), and the other end of the cable is connected to a predetermined device (not shown). Each measurement sensor 471 and the predetermined device can perform communication via the cable.

The predetermined device is, for example, a computer, and receives and acquires a measurement result signal (a biological signal) output from each of the plurality of measurement sensors 471 and executes a predetermined process on the acquired biological signal. The predetermined process may be any process and may be, for example, a process of housing the acquired biological signal in the housing portion, a process of performing predetermined calculation on the acquired biological signal, or the like.

In the present embodiment, the hole portion 511 of the sensor housing portion 461 has a region through which plurality of cables can pass.

Also, in the present embodiment, the sensor holder 321 has a configuration that does not block the hole portion 511 of the sensor housing portion 461 so that the plurality of cables can be connected to the predetermined device.

Here, for example, the plurality of cables may pass through a location other than the hole portion 511 of the sensor housing portion 461. In this case, the hole portion 511 of the sensor housing portion 461 may not be provided.

Also, for example, each measurement sensor 471 and a predetermined device (for example, a computer) may perform wireless communication without including a wired cable. In this case, the hole portion 511 of the sensor housing portion 461 may not be provided.

As described above, in the biological signal measurement device 301 according to the present embodiment, for example, as in the case of the first embodiment, it is possible to suppress the influence of noise derived from the body motion of the test subject (the subject in the present embodiment) on the measurement result of the biological signal.

In the biological signal measurement device 301 according to the present embodiment, it is possible to suppress the influence of noise derived from the body motion of the subject superimposed on the measurement result of the measurement sensor 471 by making an arrangement in which the sensor holder 321 and the measurement sensor 471 do not come into contact with the subject in a state in which the subject is sitting in the chair 311.

Here, in the biological signal measurement device 301 according to the present embodiment, the recess 414 is provided on the back surface of the chair 311 and at least a part (or all) of each of a plurality of measurement sensors 471 is arranged inside of the recess 414. When the biological signal is measured (when the state is the used state), the sensor holder 321, the measurement sensor 471, and the chair 311 have a completely physically separate structure and are arranged so that they do not come into contact with each other.

With such an arrangement, a configuration in which the body motion of the subject is not transmitted to the measurement sensor 471 is implemented and the noise (body motion noise) derived from the body motion is prevented from being superimposed on the measurement result.

Also, it is possible to make the measurement sensor 471 close to the body of the subject by arranging at least a part of the measurement sensor 471 inside of the recess 414.

Thus, in the biological signal measurement device 301 according to the present embodiment, for example, it is possible to shorten a distance between the subject and the measurement sensor 471 while preventing noise derived from the body motion of the subject from being superimposed on the measurement result of the measurement sensor 471.

Also, in the biological signal measurement device 301 according to the present embodiment, for example, the position of the measurement sensor 471 can be arranged at an appropriate position in accordance with the physique of the subject or a signal of interest thereof.

Here, the signal of interest is a signal (a biological signal) desired to be measured and may be referred to as a target signal or the like.

For example, at least one or more of the plurality of measurement sensors 471 are arranged inside of the recess 414.

For example, for all of the plurality of measurement sensors 471, at least a part of each measurement sensor 471 is arranged inside of the recess 414. The part (a part of each measurement sensor), for example, may be common to all of the plurality of measurement sensors 471.

As an example, as in the present embodiment, a shape that protrudes from the periphery closer to the center of the array-shaped portion may be used as a shape of a housing surface of the sensor housing portion that houses a plurality of measurement sensors in an array shape. As a specific example, a spherical shape may be used. In this case, for example, an arrangement form in which some measurement sensors near the center of the array-shaped portion are partially or wholly arranged inside of the recess 414 and other measurement sensors in the vicinity are arranged outside of the recess may be used.

In the biological signal measurement device 301 according to the present embodiment, a plurality of measurement sensors 471 are used, so that it is generally possible to easily capture biological signals.

In addition, the biological signals measured by each of the plurality of measurement sensors 471, for example, may be processed separately, averaged, or the like, and a process for a result of averaging or the like (a process for a result of averaging a plurality of biological signals or the like) may be performed.

Here, a case where one sensor holder 321 is used has been described in the present embodiment, but the number of sensor holders may be two or more.

Also, various arrangements may be used as the arrangement of the sensor holder 321 and the arrangement of the measurement sensor 471.

Although the present embodiment shows a configuration in which a plurality of measurement sensors are arranged in an array shape, an arrangement form of the plurality of measurement sensors is not limited thereto. Any other arrangement form may be used.

Third Embodiment

[Biological Signal Measurement Device Including Hole Cover]

A case where a biological signal measurement device 301 includes a hole cover 611 will be described with reference to FIGS. 10 to 14.

Here, a case where the biological signal measurement device 301 shown in FIGS. 4 to 9 further includes the hole cover 611 will be described with reference to the example of FIGS. 10 to 14.

Figure 10:
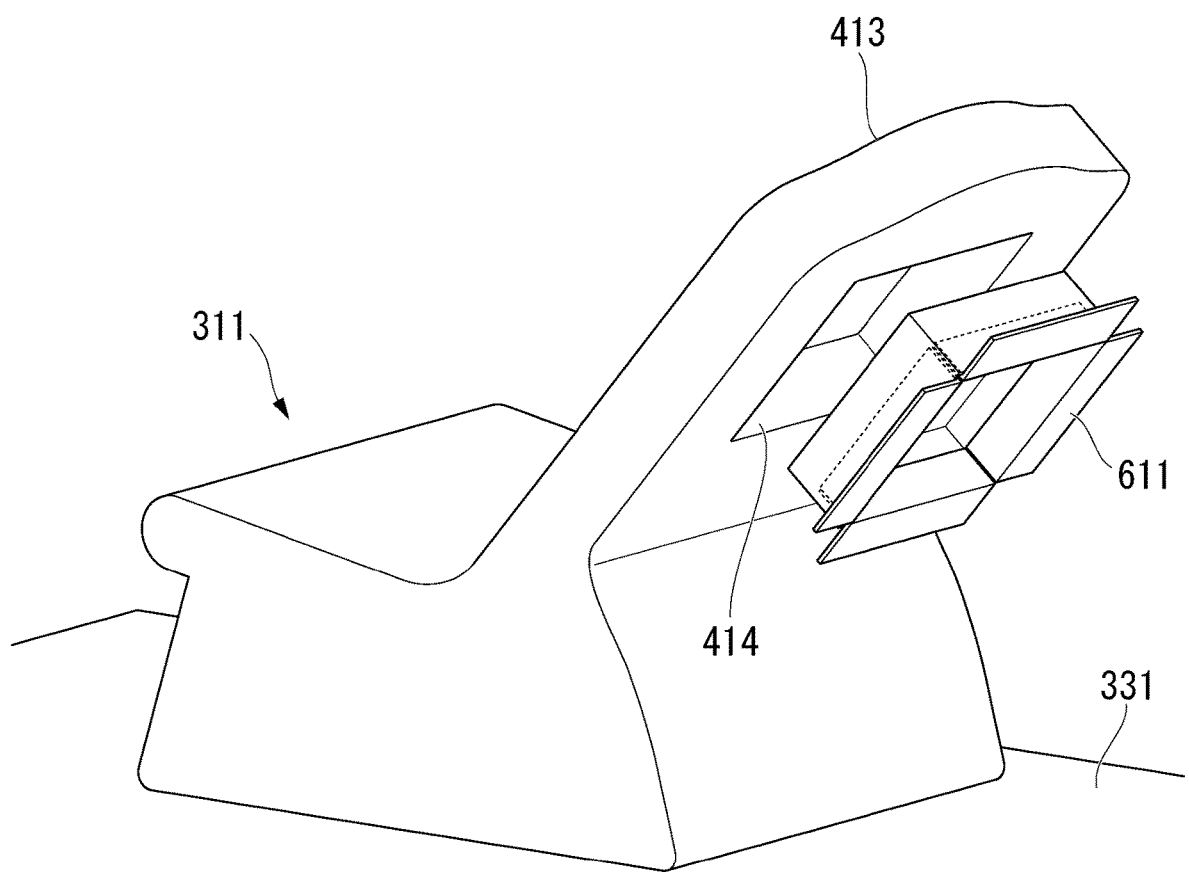
FIG. 10 is a diagram showing an example of a state in which a chair and a hole cover of a biological signal measurement device according to an embodiment (a third embodiment) are viewed from below the back surface.
Figure 11:
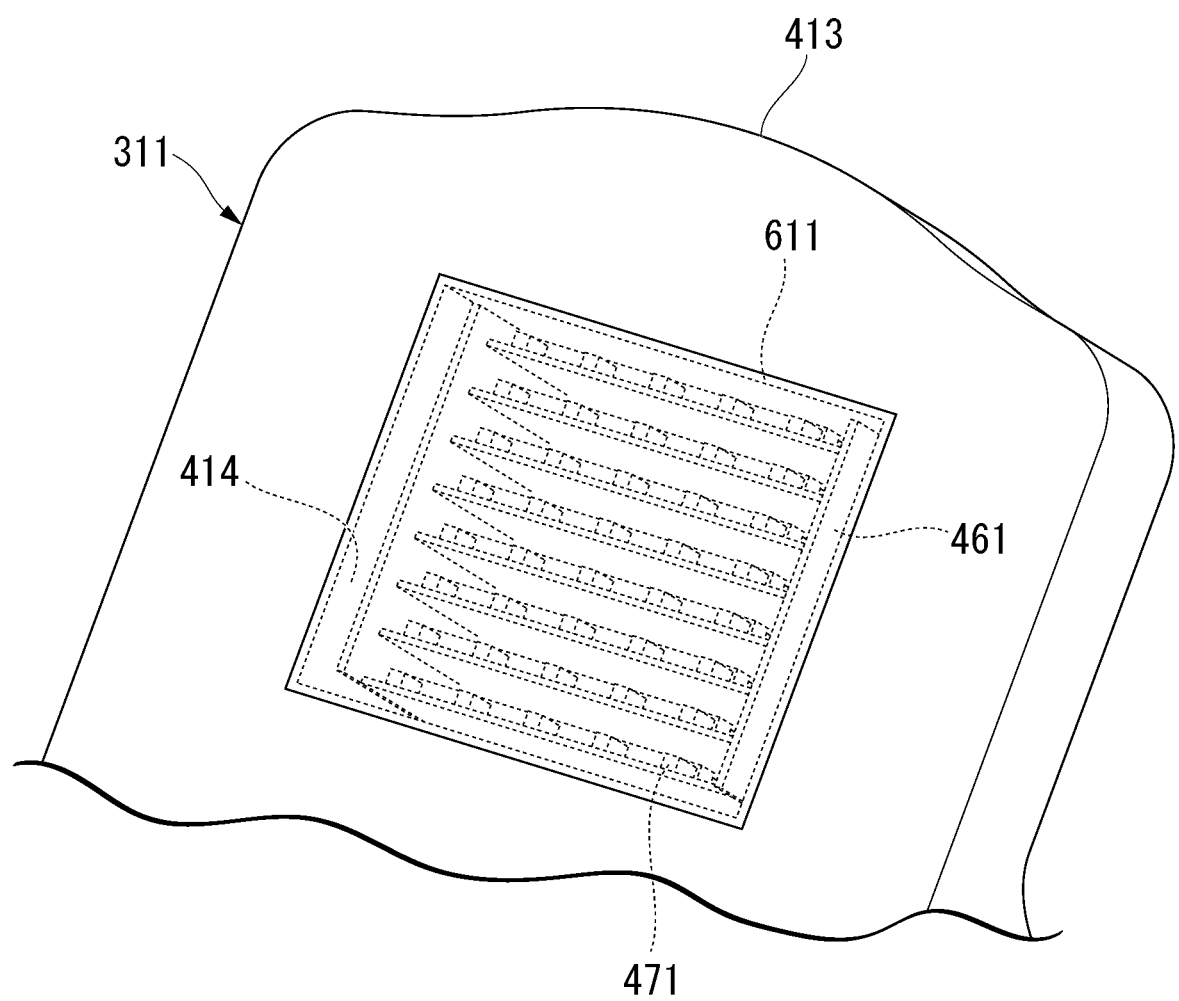
FIG. 11 is a diagram showing an example of a configuration near a recess of the biological signal measurement device according to the embodiment (the third embodiment).
Figure 12:
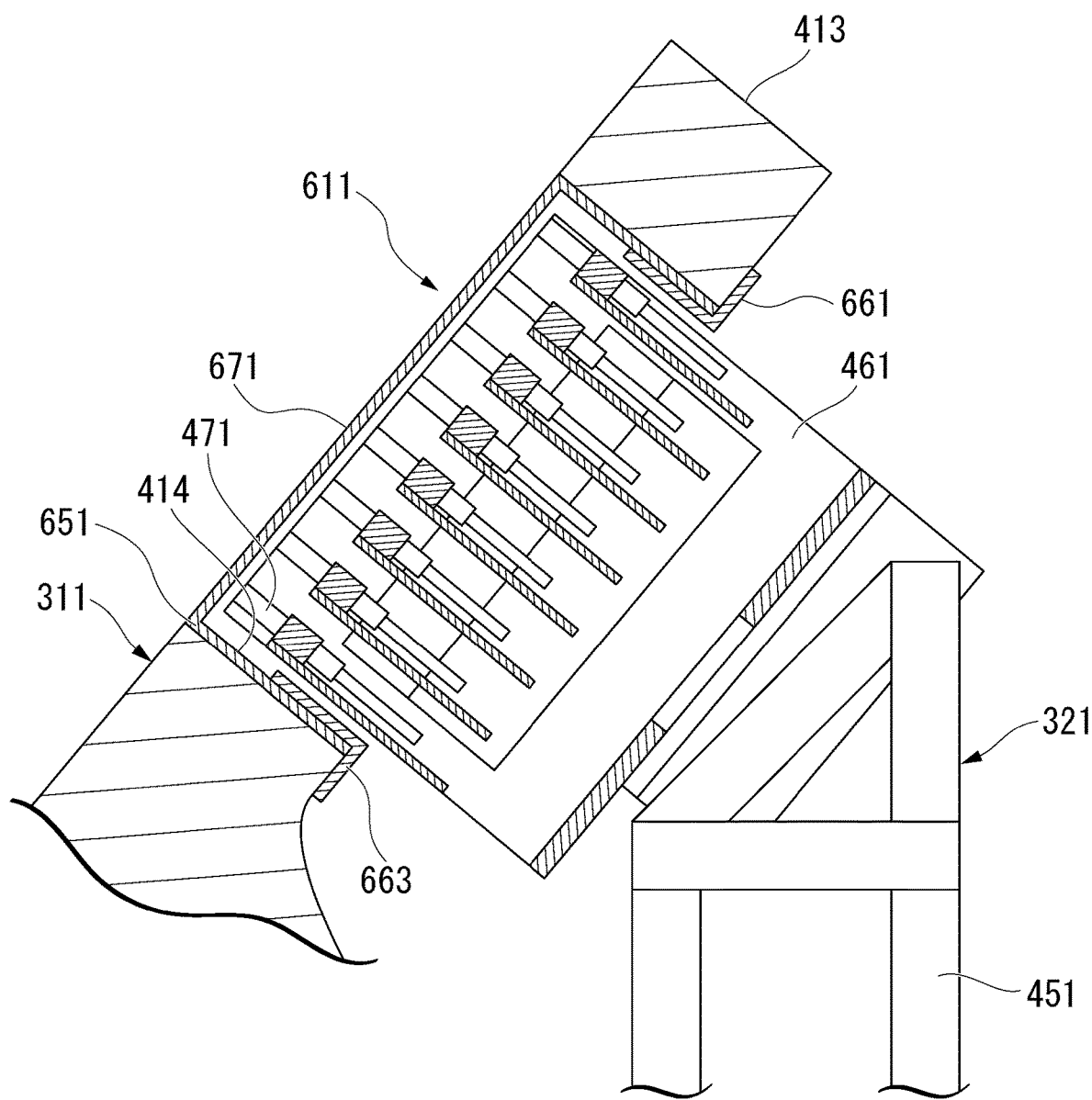
FIG. 12 is a diagram showing an example of a state of a cross-sectional viewed from a side surface near the recess of the biological signal measurement device according to the embodiment (the third embodiment).
Figure 13:
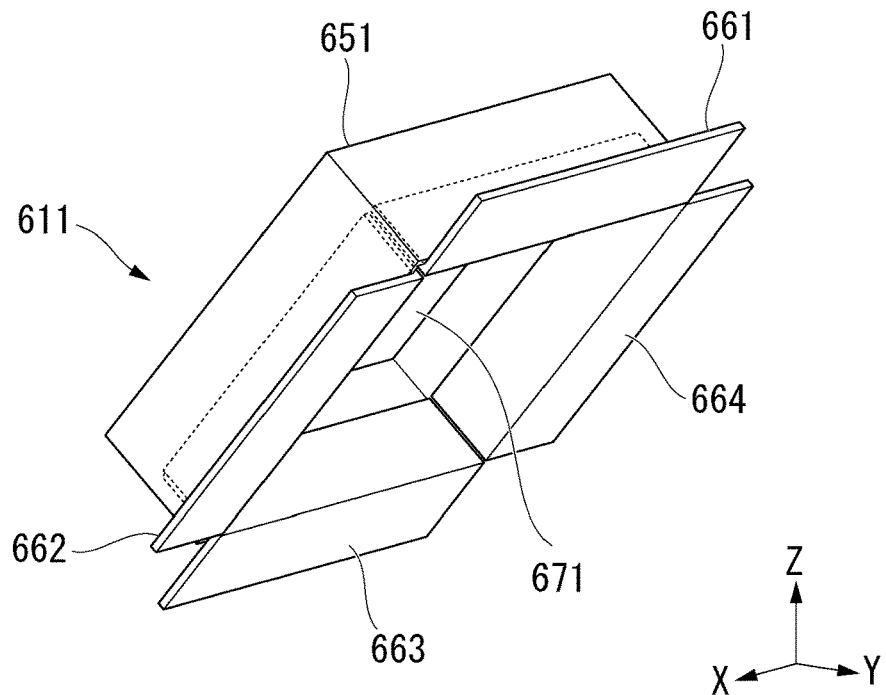
FIG. 13 is a diagram showing an example of a state in which the hole cover is obliquely viewed from below a back surface according to the embodiment (the third embodiment).
Figure 14:
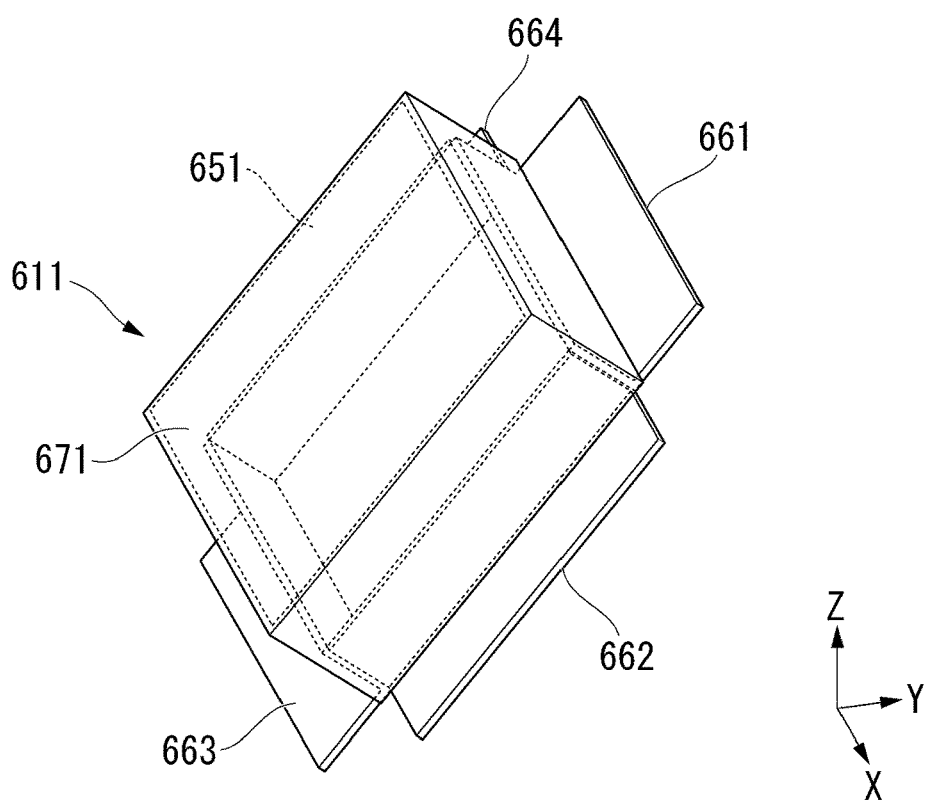
FIG. 14 is a diagram showing an example of a state in which the hole cover is obliquely viewed from above an upper surface according to the embodiment (the third embodiment).

In addition, in the example of FIGS. 10 to 11, in order to simplify the illustration, the illustration of reference signs denoting detailed components of the hole cover 611 will be omitted. In FIGS. 12 to 14, the detailed components of the hole cover 611 will be described using the reference signs.

FIG. 10 is a diagram showing an example of a state in which the chair 311 and the hole cover 611 of the biological signal measurement device 301 according to the embodiment (the third embodiment) are viewed from below the back surface.

In FIG. 10, an XYZ Cartesian coordinate system similar to that of FIG. 4 is shown.

In the example of FIG. 10, the state in which the hole cover 611 is disassembled from the chair 311 is shown for convenience of description.

The hole cover 611 is fitted into the recess 414 of the backrest portion 413 of the chair 311 from below the backrest portion 413 of the chair 311. Also, the hole cover 611 becomes a support portion that supports the subject while the subject is sitting in the chair 311. In the present embodiment, the hole cover 611 is configured with the strength of a degree to which a relevant part of the subject (near the subject's back in the present embodiment) can be supported together with a peripheral portion of the hole cover 611 in the chair 311.

Here, the chair 311 and the hole cover 611 have a configuration that they can be attached and detached in the present embodiment, but the chair 311 and the hole cover 611 may be fixedly integrated as another example.

In addition, the hole cover 611, for example, may be regarded as a component of the chair 311 or may be regarded as a component independent of the chair 311.

FIG. 11 is a diagram showing an example of a configuration near the recess 414 of the biological signal measurement device 301 according to the embodiment (the third embodiment).

Here, in FIG. 11, for the convenience of illustration, the upper surface portion of the hole cover 611 is transparently illustrated and a state of the sensor housing portion 461 and the measurement sensor 471 located inside of the recess 414 is shown. Although the upper surface portion of the hole cover 611 may be made of a transparent member, the upper surface portion of the hole cover 611 is made of an opaque member in the present embodiment. In the present embodiment, the recess 414 is a hole portion that penetrates the upper surface and the lower surface of the backrest portion 413.

In addition, the upper surface portion of the hole cover 611, for example, may be referred to as a front surface portion or the like.

FIG. 12 is a diagram showing an example of a state of a cross-section viewed from the side surface near the recess 414 of the biological signal measurement device 301 according to the embodiment (the third embodiment). The cross-section is a cross-section near the center of the chair 311 for a width direction (for example, a direction parallel to the X-axis).

Here, the sensor housing portion 461 and the plurality of measurement sensors 471 located inside of the recess 414 are arranged at a position where they do not come into contact with the hole cover 611. That is, the sensor holder 321 and the plurality of measurement sensors 471 (the sensor array in the present embodiment) are arranged at a position where they do not come into contact with the hole cover 611, and there is a gap therebetween.

<Hole Cover>

FIG. 13 is a diagram showing an example of a state in which the hole cover 611 is obliquely viewed from below the back surface according to the embodiment (the third embodiment).

FIG. 14 is a diagram showing an example of a state in which the hole cover 611 is obliquely viewed from above the upper surface according to the embodiment (the third embodiment).

FIGS. 13 and 14 each show an XYZ Cartesian coordinate system similar to that of FIG. 4. In addition, in the examples of FIGS. 13 and 14, the XYZ Cartesian coordinate system is shown for a state in which the hole cover 611 is attached to the chair 311.

The hole cover 611 schematically includes a frame portion 651 and four L-shaped portions 661 to 664.

The frame portion 651 has a shape that fits inside of the recess 414 of the backrest portion 413 of the chair 311.

In the present embodiment, the frame portion 651 has a surface (an upper surface portion 671) on the upper surface side, and the back surface side becomes an opening. The opening is a portion surrounded by the upper surface portion 671 and four side surfaces (side surface portions) on the side surface side connected to each of the four sides provided in the upper surface portion 671.

Although the upper surface portion 671 is integrated with the frame portion 651 and is a part of the frame portion 651 in the present embodiment, a case where the upper surface portion 671 is separate from a frame portion (here, a portion obtained by excluding the upper surface portion 671 from the frame portion 651) may be conceived as another example.

In the present embodiment, the frame portion 651 is a portion of the frame having the upper surface portion 671 with a square (or substantially square) shape.

The frame portion 651 has a plate-shaped member (a member of a side surface portion) at a position of each of the four sides of the square, and the square (the upper surface portion 671) and has a hollow inner portion surrounded by the four side surface portions. The plate-shaped member is a member constituting the side surface of the frame. The surface of the plate-shaped member (the surface facing the outside of the frame and the surface facing the inside thereof) has, for example, a rectangular (or substantially rectangular) shape.

In a state in which the frame portion 651 is fitted to the recess 414 of the chair 311, the surface of one of the four plate-shaped members (the surface facing the outside of the frame) is in contact with the inner surface of the recess 414 (the inner surface of the recess 414). Also, in this state, the upper surface portion 671 blocks the upper surface side of the recess 414 of the chair 311 and forms the upper surface portion of the backrest portion 413. In this state, when the subject sits in the chair 311, the subject's back is also supported by the hole cover 611 (mainly, the upper surface portion 671).

One surface of the L-shaped portions 661 to 664 is connected to the other surface (the surface facing the inside of the frame) of the four plate-shaped members of the frame portion 651.

In the L-shaped portions 661 to 664, for example, two plate-shaped portions intersecting each other at a predetermined angle (for example, 90 degrees) are connected in an L-shape.

An arrangement is made so that one surface of one L-shaped plate-shaped portion of the L-shaped portions 661 to 664 is connected to the other surface (the surface facing the inside of the frame) of each of the four plate-shaped members of the frame portion 651 and the other L-shaped plate-shaped portion extends to the outside of the frame portion 651 (a non-hollow side of the frame portion 651).

In the present embodiment, when viewed from a viewpoint in the hollow direction of the hollow portion of the frame portion 651, the other L-shaped plate-shaped portion of each of the L-shaped portion 661 to 664 is arranged to extend outward from each side of the square (or substantially square) of the frame portion 651.

In a state in which the frame portion 651 is fitted to the recess 414 of the chair 311, one surface of the other plate-shaped portion (the side surface facing the back surface of the backrest portion 413 of the chair 311) comes into contact with the back surface of the backrest portion 413 of the chair 311.

In the present embodiment, in a state in which the frame portion 651 of the hole cover 611 is fitted to the recess 414 of the chair 311, it has a shape that does not fall out of the recess 414 without an external force. That is, in the present embodiment, according to a manual operation of an operator (person) of the biological signal measurement device 301 or the like, the frame portion 651 of the hole cover 611 is fitted and attached to the recess 414 of the chair 311 and the frame portion 651 of the hole cover 611 attached to the recess 414 of the chair 311 is removed.

As another example, the biological signal measurement device 301 may include a fixing tool for fixing the hole cover 611 and the chair 311 in a state in which the frame portion 651 of the hole cover 611 is fitted to the recess 414 of the chair 311.

As the fixing tool, any fixing tool may be used and, for example, a screw, a locking portion, or an adhesive may be used.

Thus, the method of fixing the chair 311 and the hole cover 611 is not particularly limited. For example, a fixing method using a screw, a fixing method using a locking portion, a fixing method using an adhesive, or the like may be used.

As described above, the biological signal measurement device 301 according to the present embodiment, for example, can obtain effects similar to those of the second embodiment, and further includes the hole cover 611.

The hole cover 611, for example, is attached to the backrest portion 413 from the back of the chair 311 and does not come into contact with the sensor holder 321 and the plurality of measurement sensors 471 (the sensor array in the present embodiment). In the present embodiment, the sensor holder 321 and the plurality of measurement sensors 471 are arranged to be physically separated from the hole cover 611 without coming into contact with the hole cover 611.

In the biological signal measurement device 301 according to the present embodiment, the body of the subject can be supported by the hole cover 611. Thereby, in the biological signal measurement device 301 according to the present embodiment, in a state in which the subject is in a stable state (a state in which shaking is small when the subject is sitting in the chair 311), the measurement sensor 471 does not come into contact with the subject, the measurement sensor 471 can be made close to the subject, and a biological signal can be measured with higher accuracy.

<Material of Hole Cover>

In the biological signal measurement device 301 according to the present embodiment, for example, the material of the hole cover 611 may be made of a non-magnetic body without using a magnetic body.

In such a configuration, for example, magnetic noise caused by vibration of a magnetic body in the hole cover can be eliminated, thereby reducing noise derived from the body motion of the subject 211 superimposed on the measurement result of the measurement sensor 471 (a magnetic signal in the present embodiment) and improving the accuracy of the measurement result of the measurement sensor 471 (the magnetic signal in the present embodiment).

Here, as the non-magnetic body, for example, a non-magnetic metal, wood, leather, or a resin such as urethane or acrylic may be used.

In addition, as another example, the material of the hole cover 611 may include a magnetic body.

In the biological signal measurement device 301 according to the present embodiment, for example, the materials of the chair 311 and the hole cover 611 may be made of a non-magnetic body without using a magnetic body.

In such a configuration, the accuracy of the measurement result (the magnetic signal in the present embodiment) of the measurement sensor 471 can be further improved.

Fourth Embodiment

[Biological Signal Measurement Device Including Chair Adjustment Portion]

A case where a biological signal measurement device 301a includes a chair adjustment portion 711 will be described with reference to FIG. 15.

Figure 15:
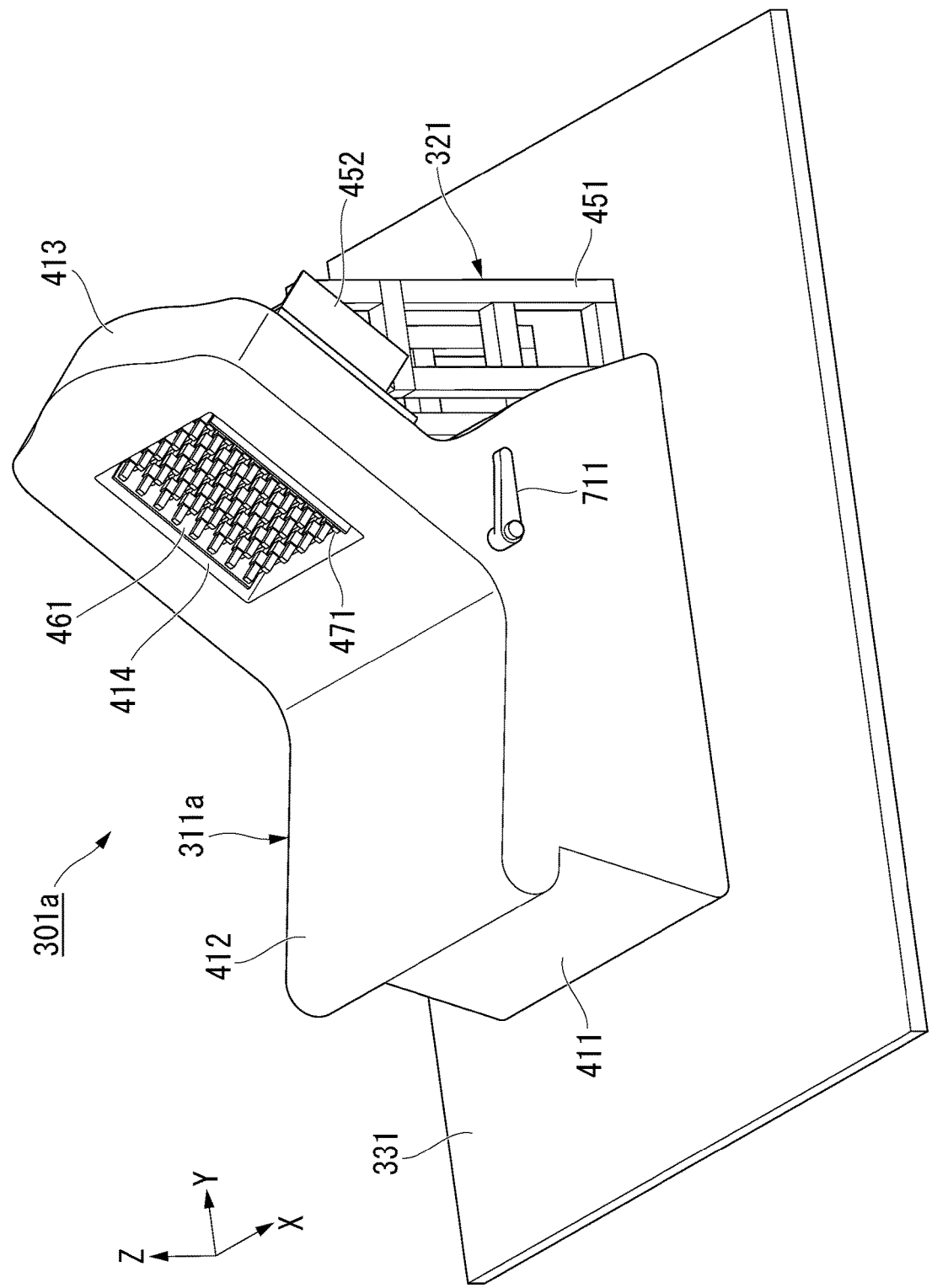
FIG. 15 is a diagram showing an example of a configuration of a biological signal measurement device according to an embodiment (a fourth embodiment).

Here, the biological signal measurement device 301a further including the chair adjustment portion 711 in a configuration similar to that of the biological signal measurement device 301 shown in FIG. 4 is shown in the example of FIG. 15.

Therefore, in the present embodiment, components similar to those of the biological signal measurement device 301 shown in FIG. 4 denoted by the same reference signs will be described.

FIG. 15 is a diagram showing an example of the configuration of the biological signal measurement device 301a according to the embodiment (the fourth embodiment).

In FIG. 15, an XYZ Cartesian coordinate system, which is a three-dimensional Cartesian coordinate system, is shown for convenience of description.

The biological signal measurement device 301a includes a chair 311a, a sensor holder 321, and a measurement sensor 471.

In the present embodiment, a state in which the chair 311a and the sensor holder 321 constituting the biological signal measurement device 301a are placed directly or indirectly (for example, via an anti-vibration portion) on an installation portion will be described as an example.

The installation portion is a place where the biological signal measurement device 301a is placed, and is, for example, a floor surface, a board surface, or the like.

In the example of FIG. 15, the installation surface is the surface of the board 331.

Here, in the present embodiment, the sensor holder 321 and the measurement sensor 471 have configurations similar to those in the example of FIG. 4.

<Chair>

The chair 311a includes a leg portion 411, a seat surface portion 412, a backrest portion 413, and a chair adjustment portion 711.

The backrest portion 413 has a recess 414.

Here, the configuration of the chair 311a in the present embodiment is schematically different from the configuration of the chair 311 shown in FIG. 4 in that a chair adjustment portion 711 is provided, and others are similar.

The chair adjustment portion 711 has, for example, a mechanism for adjusting the angle (inclination) of the upper surface of the backrest portion 413 with respect to the seat surface of the seat surface portion 412 of the chair 311a.

In the example of FIG. 15, the chair adjustment portion 711 has an operation portion such as a lever. Also, the chair adjustment portion 711 has a mechanism that can adjust the angle of the backrest portion 413 of the chair 311a by manually operating the operation portion by an operator or the like (for example, he or she may be a subject).

Although such an operation portion is located near the connection between the seat surface portion 412 and the backrest portion 413 and is located on the left side (the left side as seen from the subject) when the subject sits in the chair 311a in the example of FIG. 15, its installation location is not limited thereto and another location may be used.

As an example, the chair adjustment portion 711 may have a mechanism that can change the angle of the upper surface of the backrest portion 413 with respect to the seat surface of the seat surface portion 412 according to a manual operation of an operator or the like (for example, he or she may be a subject) and may have an operation portion (for example, a lever serving as a stopper or the like) for switching the state between a state in which the change is possible and a state in which the change is impossible. In this case, the subject or the like can change the angle by switching the state to the state in which the change is possible through the operation portion and adjust the angle by switching the state to the state in which the change is impossible through the operation portion after an adjustment to any angle.

As another example, the chair adjustment portion 711 has a mechanism that can change the angle of the upper surface of the backrest portion 413 with respect to the seat surface of the seat surface portion 412 through an electric device (for example, a motor or the like) and may have an operation portion for issuing an instruction to make the change. In this case, the subject or the like can adjust the angle by operating the operation portion.

Here, an example in which the chair adjustment portion 711 can adjust the angle of the backrest portion 413 of the chair 311a is shown, but the chair adjustment portion 711 may be able to adjust other adjustment targets in the chair 311a and may be able to adjust two or more adjustment targets.

The other adjustment target may be, for example, a position in the height direction of the seat surface portion 412 or the like. In addition, as a mechanism for making various types of adjustments, for example, any mechanism may be used like a mechanism for adjusting the angle of the backrest portion 413.

As an example, as another adjustment target, the position of the chair 311a (the position of the chair 311a itself) may be used. In this case, a rail mechanism capable of moving the position of the chair 311a in one or more predetermined directions may be used. For example, one or both of a width direction (for example, a direction parallel to the X-axis) and a longitudinal direction (for example, a direction parallel to the Y-axis) may be used as the predetermined direction.

As described above, the biological signal measurement device 301a according to the present embodiment can adjust the arrangement of a part or all of the chair 311a (the chair 311a itself). Thereby, for example, the subject can perform measurement in a comfortable posture and the biological signal can be measured in a stable state.

Here, the chair adjustment portion 711 (an example of the placement portion adjustment portion) adjusts, for example, at least one of a position and an angle of a part of the chair 311a.

Fifth Embodiment

[Biological Signal Measurement Device Including Measurement Sensor Adjustment Portion]

A case where a biological signal measurement device 301b includes a measurement sensor adjustment portion 751 will be described with reference to FIG. 16.

Figure 16:
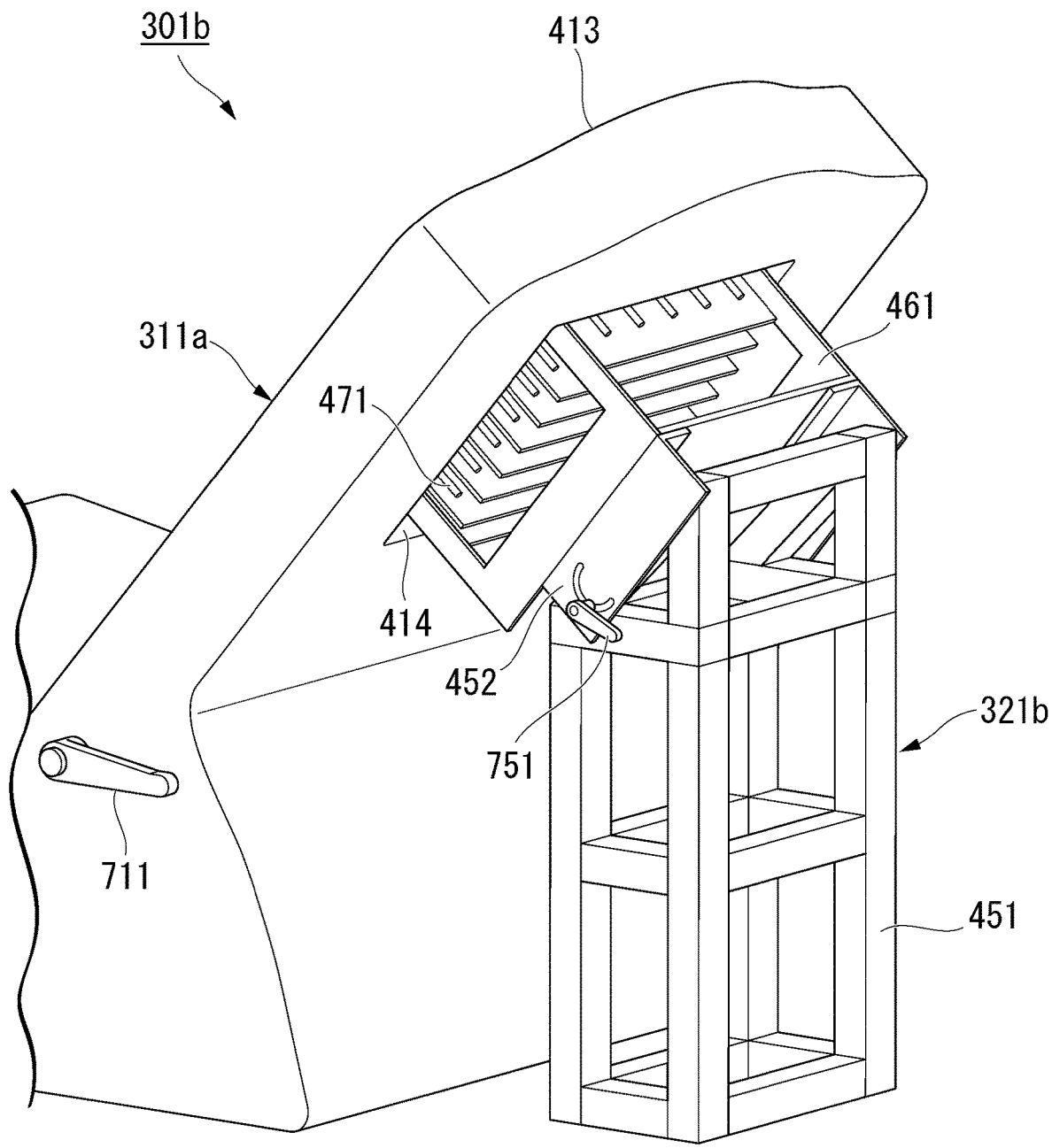
FIG. 16 is a diagram showing an example of a configuration of a biological signal measurement device according to an embodiment (a fifth embodiment).

Here, in the example of FIG. 16, the biological signal measurement device 301b further including a measurement sensor adjustment portion 751 in a configuration similar to that of the biological signal measurement device 301a shown in FIG. 15 is shown.

Therefore, in the present embodiment, components similar to those of the biological signal measurement device 301a shown in FIG. 15 denoted by the same reference signs will be described.

FIG. 16 is a diagram showing an example of a configuration of the biological signal measurement device 301b according to an embodiment (a fifth embodiment).

In FIG. 16, for convenience of description, an XYZ Cartesian coordinate system, which is a three-dimensional Cartesian coordinate system, is shown.

In addition, in the example of FIG. 16, for convenience of description, as a part of the configuration of the biological signal measurement device 301b, an example of a state in which a part of a chair 311a and a part of a sensor holder 321b are obliquely viewed from below is shown.

The biological signal measurement device 301b includes the chair 311a, the sensor holder 321b, and a measurement sensor 471.

In the present embodiment, a state in which the chair 311a and the sensor holder 321b constituting the biological signal measurement device 301b are placed directly or indirectly (for example, via an anti-vibration portion) on an installation portion will be described as an example.

The installation portion is a place where the biological signal measurement device 301b is placed and is, for example, a floor surface, a board surface, or the like.

In the example of FIG. 16, the installation surface is a surface of a board 331 (not shown in FIG. 16).

Here, the chair 311a and the measurement sensor 471 in the present embodiment have configurations similar to those in the example of FIG. 15.

<Sensor Holder>

The sensor holder 321b includes a base portion 451, a support portion 452, a sensor housing portion 461, and a measurement sensor adjustment portion 751.

Here, the configuration of the sensor holder 321b in the present embodiment is schematically different from the configuration of the sensor holder 321 shown in FIGS. 15 (and 4) in that the measurement sensor adjustment portion 751 is provided, and others are similar.

The measurement sensor adjustment portion 751 may have a mechanism for adjusting the angle (inclination) of the upper surface (upper surface) of the support portion 452 (two support portions on both sides in the present embodiment), for example, in the upward/downward direction (or in the horizontal direction). In the present embodiment, when the angle of the upper surface of the support portion 452 is adjusted, the angle of the sensor housing portion 461 provided in the support portion 452 is adjusted accordingly and the angle of the measurement sensor 471 housed in the sensor housing portion 461 is adjusted accordingly.

In the example of FIG. 16, the measurement sensor adjustment portion 751 has an operation portion such as a lever. Also, the measurement sensor adjustment portion 751 has a mechanism for allowing the angle of the upper surface of the support portion 452 to be adjusted by manually operating the operation portion through an operator or the like.

Although such an operation portion is provided on the support portion 452 and arranged on the surface of the left side (the left side as seen from the subject) when the subject sits in the chair 311a in the support portion 452 in the example of FIG. 16, the installation location is not limited thereto and another location may be used.

As an example, the measurement sensor adjustment portion 751 may have a mechanism that can change the angle of the upper surface of the support portion 452 in the upward/downward direction according to a manual operation of an operator or the like and have an operation portion of switching the state between the state in which the change is possible and the state in which the change is impossible (for example, a lever serving as a stopper). In this case, the operator or the like can change the angle to switch the state to the state in which the change is possible according to the operation portion and can adjust the angle by switching the state to the state in which the change is impossible through the operation portion after an adjustment to any angle.

As another example, the measurement sensor adjustment portion 751 has a mechanism that can change the angle of the upper surface of the support portion 452 in the upward/downward direction by an electric device (for example, a motor), and may have an operation portion for issuing an instruction to make the change. In this case, the operator or the like can adjust the angle by operating the operation portion.

Here, an example in which the measurement sensor adjustment portion 751 can adjust the angle of the upper surface of the support portion 452 of the sensor holder 321b (i.e., the angle at which the measurement sensor 471 is facing) has been described, but the measurement sensor adjustment portion 751 can adjust another adjustment target related to the measurement sensor 471. Also, for example, it is possible to adjust two or more adjustment targets.

The other adjustment target may be, for example, a position in a height direction of the support portion 452 (the upper surface thereof) (i.e., the position in the height direction of the measurement sensor 471). As the mechanism for making various types of adjustments, for example, any mechanism may be used like a mechanism for adjusting the angle of the upper surface of the support portion 452.

As an example, the position of the sensor holder 321b (the position of the sensor holder 321b itself) may be used as the other adjustment target. In this case, a rail mechanism in which the position of the sensor holder 321b can be moved in one or more predetermined directions may be used. For example, one or both of the width direction (for example, the direction parallel to the X-axis) and the longitudinal direction (for example, the direction parallel to the Y-axis) may be used as the predetermined direction.

Although a case where the measurement sensor adjustment portion 751 changes the angle of the upper surface of the support portion 452 of the sensor holder 321b is shown in the present embodiment, a configuration in which the angle of the base portion 451 of the sensor holder 321b, the angle of the sensor housing portion 461, or the like is changed may be used as another example.

As described above, the biological signal measurement device 301b according to the present embodiment can adjust the arrangement of the measurement sensor 471. Thereby, for example, the subject can perform measurement in a comfortable posture, and the biological signal can be measured in a stable state.

In the biological signal measurement device 301b according to the present example, the measurement sensor 471 can be freely arranged inside of the recess 414 of the chair 311a or the like and a position or an angle of the measurement sensor 471 can be adjusted in accordance with a physique of the subject or a position of a measurement site (for example, a body part such as the heart) of the biological signal.

Here, the measurement sensor adjustment portion 751 directly or indirectly adjusts, for example, at least one of the positions or angles of the measurement sensor 471.

Sixth Embodiment

[Biological Signal Measurement Device Including Reference Sensor Holder and Reference Sensor]

A case where a biological signal measurement device includes a reference sensor holder and a reference sensor will be described with reference to FIGS. 17 to 18.

Figure 17:
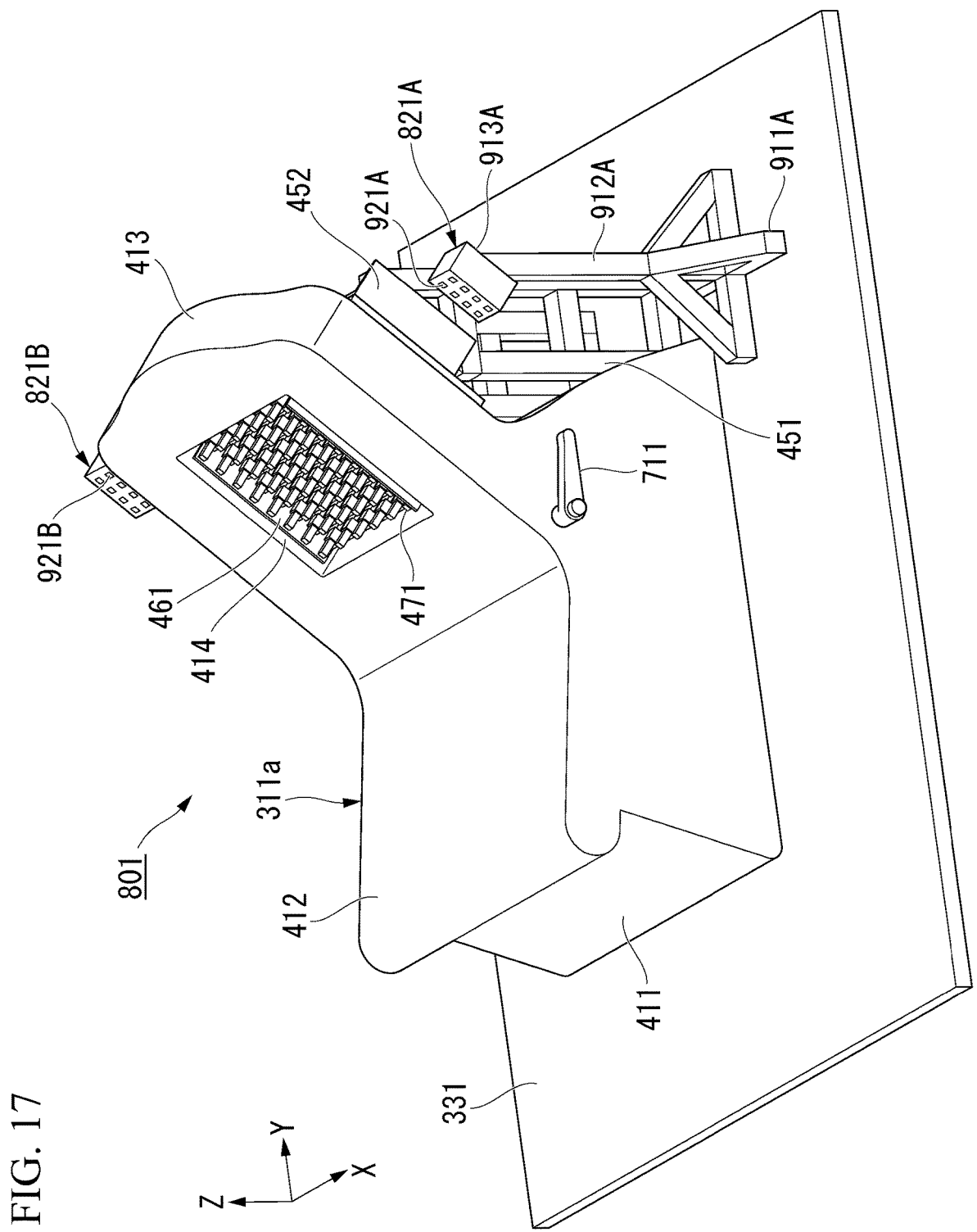
FIG. 17 is a diagram showing an example of a configuration of a biological signal measurement device according to an embodiment (a sixth embodiment).
Figure 18:
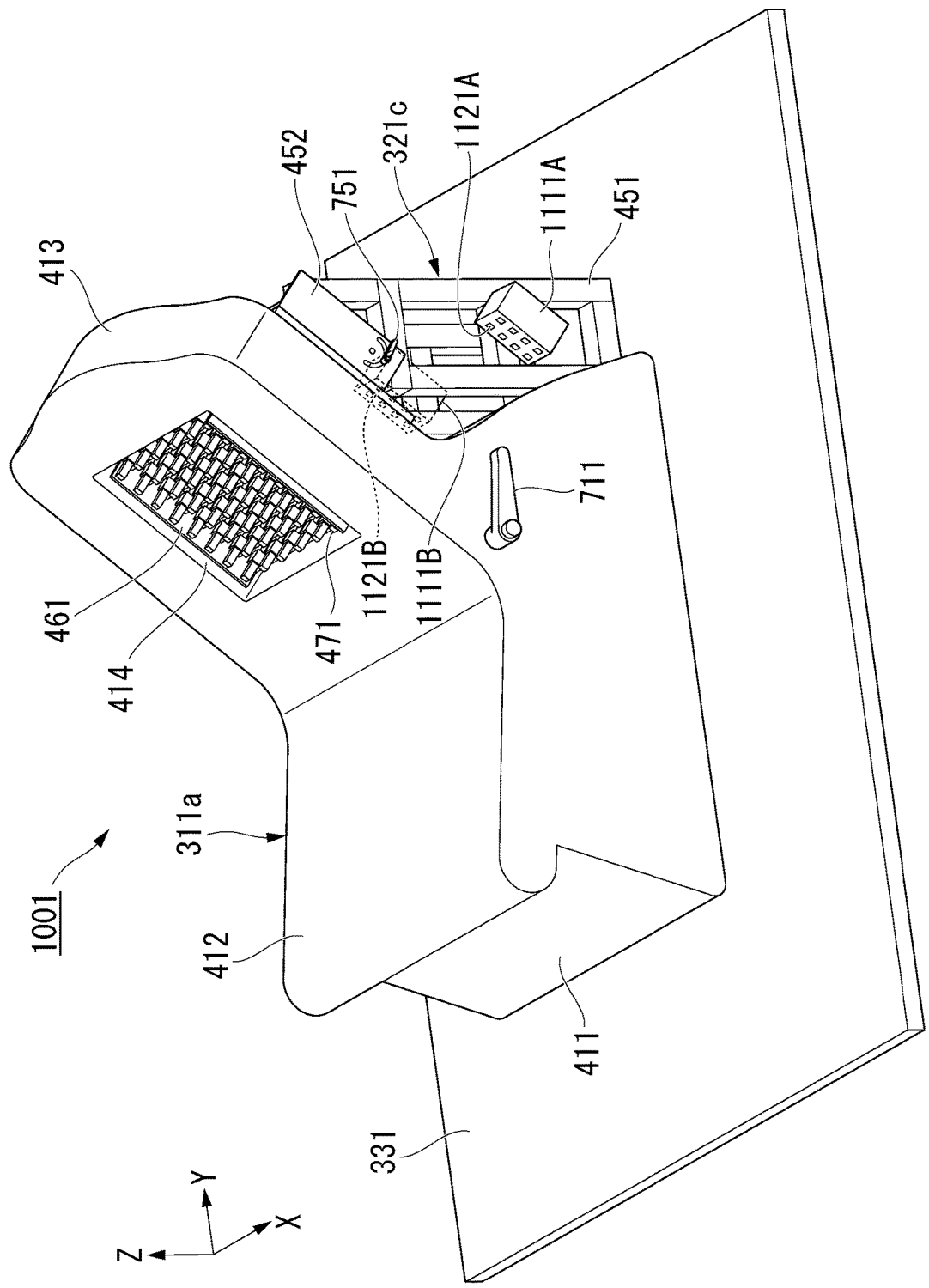
FIG. 18 is a diagram showing another example of the configuration of the biological signal measurement device according to the embodiment (the sixth embodiment).

Here, in the example of FIGS. 17 to 18, a biological signal measurement device further including a reference sensor holder and a reference sensor in a configuration similar to that of the biological signal measurement device 301b shown in FIG. 16 is shown.

Therefore, in the present embodiment, components similar to those of the biological signal measurement device 301b shown in FIG. 16 denoted by the same reference signs will be described.
<Example of Biological Signal Measurement Device>

FIG. 17 is a diagram showing an example of a configuration of a biological signal measurement device 801 according to an embodiment (a sixth embodiment).

In FIG. 17, an XYZ Cartesian coordinate system, which is a three-dimensional Cartesian coordinate system, is shown for convenience of description.

The biological signal measurement device 801 includes a chair 311a, a sensor holder 321b, a measurement sensor 471, two reference sensor holders 821A and 821B, and reference sensors 921A and 921B held by the reference sensor holders 821A and 821B.

In the present embodiment, a state in which the chair 311a, the sensor holder 321b, and the reference sensor holders 821A and 821B constituting the biological signal measurement device 801 are placed directly or indirectly (for example, via an anti-vibration portion) on an installation portion will be described as an example.

The installation portion is a place where the biological signal measurement device 801 is placed, and is, for example, a floor surface, a board surface, or the like.

In the example of FIG. 17, an installation surface is a surface of a board 331.

Here, in the present embodiment, the chair 311a, the sensor holder 321b, and the measurement sensor 471 have configurations similar to those in the example of FIG. 16.

In the present embodiment, the configuration of the reference sensor holder 821A and the configuration of the reference sensor holder 821B are similar to each other and the reference sensor holder 821A will be representatively described.

Also, in the present embodiment, the configuration of the reference sensor 921A and the configuration of the reference sensor 921B are similar to each other and the reference sensor 921A will be representatively described.

<Reference Sensor Holder>

The reference sensor holder 821A includes a leg portion 911A, a shaft portion 912A, and a reference sensor housing portion 913A.

The leg portion 911A is a base portion and is in contact with the installation surface (the surface of the board 331 in the example of FIG. 17).

In the present embodiment, the leg portion 911A has a four-legged configuration, but is not limited thereto, and any configuration may be used.

The shaft portion 912A is a rod-shaped portion. One end of the shaft portion 912A is connected to the leg portion 911A and the other end of the shaft portion 912A is connected to a back surface of the reference sensor housing portion 913A.

The reference sensor housing portion 913A is a housing portion capable of housing a plurality of reference sensors.

In the present embodiment, the reference sensor housing portion 913A schematically has a cuboid shape and a mechanism (housing mechanism) for housing a plurality of reference sensors (for example, in an array shape or another arrangement) is provided on one surface of the cuboid. In the present embodiment, the housing mechanism of the plurality of reference sensors is an array in which a plurality of measurement sensors are arranged in parallel to one of orthogonal sides of the housing surface of the reference sensor housing portion 913A and in parallel to the other side and, for example, is an array in which reference sensors are regularly arranged in a grid shape. In addition, thus, a plurality of sensors (here, reference sensors) arranged in an array shape may be referred to as a sensor array.

Here, the housing mechanism of the reference sensor housing portion 913A is a mechanism in which each of the plurality of reference sensors can be attached and detached, but the housing mechanism of the reference sensor housing portion 913A and the reference sensor may be fixedly integrated as another example.

In the example of FIG. 17, the surface (back surface) facing the housing surface of the reference sensor housing portion 913A is attached to the other end (upper end) of the shaft portion 912A.

In the present embodiment, the housing surface of the reference sensor housing portion 913A is arranged so that the height position of one side of the pair is above the position of the height of the other side in the horizontal direction. That is, in the side view, the housing surface of the reference sensor housing portion 913A is oblique in the upward/downward direction.

Here, the shaft portion 912A and the reference sensor housing portion 913A may have, for example, a configuration in which they can be attached to and detached from each other or they may be integrated.

<Reference Sensors>

In the present embodiment, a plurality of reference sensors are attached to the housing surface of the reference sensor housing portion 913A.

In the present embodiment, in the example of FIG. 17, only one reference sensor 921A of the plurality of reference sensors is denoted by a reference sign.

The reference sensor 921A has a function of measuring a predetermined reference signal. In the present embodiment, the reference sensor 921A is a magnetic sensor that measures a magnetic signal in an environment.

Although a predetermined surface in the reference sensor 921A is arranged to face the outside of the housing surface of the reference sensor housing portion 913A in the present embodiment, other forms may be used as an arrangement form.

In the present embodiment, a reference signal is a signal that becomes environmental noise to a signal of interest (a biological signal) to be measured by the measurement sensor 471.

Here, the reference sensor housing portion 913A included in the reference sensor holder 821A has been described in the present embodiment, but a case where the reference sensor housing portion 913A is separate from the reference sensor holder 821A may be conceived as another example.

<Arrangement of Chair, Sensor Holder, and Reference Sensor Holder>

In the present embodiment, the chair 311a, the sensor holder 321b (and a plurality of measurement sensors 471), the reference sensor holder 821A (and a plurality of reference sensors 921A), and the reference sensor holder 821B (and a plurality of reference sensors 921B) are physically separate and completely independent.

Also, these are arranged so that they do not come into contact with each other.

In the example of FIG. 17, the reference sensor holder 821A (and a plurality of reference sensors 921A) is located on the left side (the left side as seen from the subject) when the subject sits in the chair 311a with respect to the position of the sensor holder 321b. Also, the reference sensor holder 821A (and a plurality of reference sensors 921A) are arranged so that the housing surface of the reference sensor housing portion 913A obliquely faces upward in the same direction as an upper surface of the backrest portion 413 (or in the vicinity thereof).

Also, in the example of FIG. 17, the reference sensor holder 821B (and a plurality of reference sensors 921B) is located on the right side (the right side as seen from the subject) when the subject sits in the chair 311a with respect to the position of the sensor holder 321b. Also, the reference sensor holder 821B (and the plurality of reference sensors 921B) is arranged so that the housing surface of the reference sensor housing portion obliquely faces upward in the same direction as the upper surface of the backrest portion 413 (or in the vicinity thereof).

<Other Examples of Biological Signal Measurement Device>

FIG. 18 is a diagram showing another example of the configuration of the biological signal measurement device 1001 according to the embodiment (the sixth embodiment).

In FIG. 18, an XYZ Cartesian coordinate system, which is a three-dimensional Cartesian coordinate system, is shown for convenience of description.

The biological signal measurement device 1001 includes a chair 311a, a sensor holder 321c, a measurement sensor 471, two reference sensor holders 1111A and 1111B, and reference sensors 1121A and 1121B held by the reference sensor holders 1111A and 1111B, respectively.

In the present embodiment, a state in which the chair 311a and the sensor holder 321c constituting the biological signal measurement device 1001 are placed directly or indirectly (for example, via an anti-vibration portion) on an installation portion will be described as an example.

The installation portion is a place where the biological signal measurement device 1001 is placed and is, for example, a floor surface, a board surface, or the like.

In the example of FIG. 18, the installation surface is a surface of the board 331.

Here, in the present embodiment, the chair 311a and the measurement sensor 471 have configurations similar to those in the example of FIG. 16.

<Sensor Holder>

The sensor holder 321c further includes two reference sensor holders 1111A and 1111B in a configuration similar to that of the sensor holder 321b shown in FIG. 16.

In the example of FIG. 18, in the sensor holder 321b, when the upper surface of the support portion 452 and its back surface are the front and back surfaces, the reference sensor holder 1111A and the reference sensor holder 1111B are provided on the two side surfaces of the base portion 451.

In the example of FIG. 18, in the base portion 451 of the sensor holder 321b, the reference sensor holder 1111A is provided on the left side (the left side from the subject) when the subject sits in the chair 311a and the reference sensor holder 1111B is provided on the right side (the right side from the subject) when the subject sits in the chair 311a.

In the present embodiment, the configuration of the reference sensor holder 1111A and the configuration of the reference sensor holder 1111B are similar to each other and the reference sensor holder 1111A will be representatively described.

Also, in the present embodiment, the configuration of the reference sensor 1121A and the configuration of the reference sensor 1121B are similar to each other and the reference sensor 1121A will be representatively described.

<Reference Sensor Holder>

In the example of FIG. 18, the reference sensor holder 1111A has a configuration similar to that of the reference sensor housing portion 913A shown in FIG. 17.

In the present embodiment, the housing surface (the housing surface of the reference sensor) of the reference sensor holder 1111A is arranged so that a height position of one side of a pair of sides is above a height position of the other side in the horizontal direction. That is, in the side view, the housing surface of the reference sensor holder 1111A is oblique in the upward/downward direction.

Here, the sensor holder 321c and the reference sensor holder 1111A may have, for example, a configuration in which they can be attached to and detached from each other, or they may be integrated.

<Reference Sensor>

In the present embodiment, a plurality of reference sensors are attached to the housing surface of the reference sensor holder 1111A.

In the present embodiment, in the example of FIG. 18, only one reference sensor 1121A of the plurality of reference sensors is denoted by a reference sign.

The reference sensor 1121A has a configuration similar to that of the reference sensor 921A shown in FIG. 17.

Although a predetermined surface of the reference sensor 1121A is arranged to face the outside of the housing surface of the reference sensor holder 1111A in the present embodiment, other forms may be used as the arrangement form.
<Arrangement of Chair, Sensor Holder, and Reference Sensor Holder>

In the present embodiment, the chair 311a and the sensor holder 321c (and the plurality of measurement sensors 471) are physically separate and completely independent.

Also, these are arranged so that they do not come into contact with each other.

Here, in the example of FIG. 18, the reference sensor holder 1111A (and a plurality of reference sensors 1121A) and the reference sensor holder 1111B (and a plurality of reference sensors 1121B) are provided in the sensor holder 321c and are physically separate from the chair 311a and completely independent.

In the example of FIG. 18, the reference sensor holder 1111A (and a plurality of reference sensors 1121A) is arranged so that the housing surface of the reference sensor holder 1111A obliquely faces upward in the same direction as an upper surface of the backrest portion 413 (or in the vicinity thereof).

Also, in the example of FIG. 18, the reference sensor holder 1111B (and a plurality of reference sensors 1121B) is arranged so that the housing surface of the reference sensor holder 1111B obliquely faces upward in the same direction as an upper surface of the backrest portion 413 (or in the vicinity thereof).

As described above, in the biological signal measurement device 801 according to the present embodiment, a reference signal can be measured by the reference sensors 921A and 921B and the noise included in the measurement result of the measurement sensor 471 can be reduced in a noise reduction method using the reference signal.

Likewise, in the biological signal measurement device 1001 according to the present embodiment, a reference signal can be measured by the reference sensors 1121A and 1121B and the noise included in the measurement result of the measurement sensor 471 can be reduced in a noise reduction method using the reference signal.

Here, in the example of the biological signal measurement device 801, the reference sensor holders 821A and 821B are separate from the sensor holders 321b.

Also, in the example of the biological signal measurement device 1001, the reference sensor holders 1111A and 1111B are integrated with the sensor holders 321c.

Also, as the reference signal, for example, a signal having only environmental noise that does not include a signal of interest (a biological signal desired to be measured) may be used.

Also, as the noise reduction method, any method may be used and signal processing such as adaptive noise cancelling (ANC) may be used. According to ANC or the like, for example, it is possible to reduce the environmental noise included in the measurement result of the measurement sensor 471.

Here, a case where two reference sensor holders are used is shown in the examples of FIGS. 17 and 18, but the number of reference sensor holders may be one or may be three or more.

Although a case where a plurality of reference sensors are used is shown in the examples of FIGS. 17 and 18, the number of reference sensors may be one.

Also, various arrangements may be used as the arrangement of the reference sensor holder and the arrangement of the reference sensor.

Although a case where the arrangement of the reference sensor holder is fixed is shown in the examples of FIGS. 17 and 18, the reference sensor holder may be used in a configuration in which the arrangement of the reference sensor can be adjusted as another example.

For example, a configuration in which the arrangement of a part of the reference sensor holder (a portion that affects the arrangement of the reference sensor) can be changed (adjusted) may be used. The arrangement may include, for example, one or both of a position and an angle.

Also, for example, a configuration in which such a change (adjustment) of the arrangement is made according to a manual operation of an operator or the like may be used or a configuration in which such a change (adjustment) of the arrangement is made by an electric device (for example, a motor) in accordance with a process in which the operator or the like operates the operation portion may be used.

Seventh Embodiment

[Modified Example of Chair in Biological Signal Measurement Device]

Figure 19:
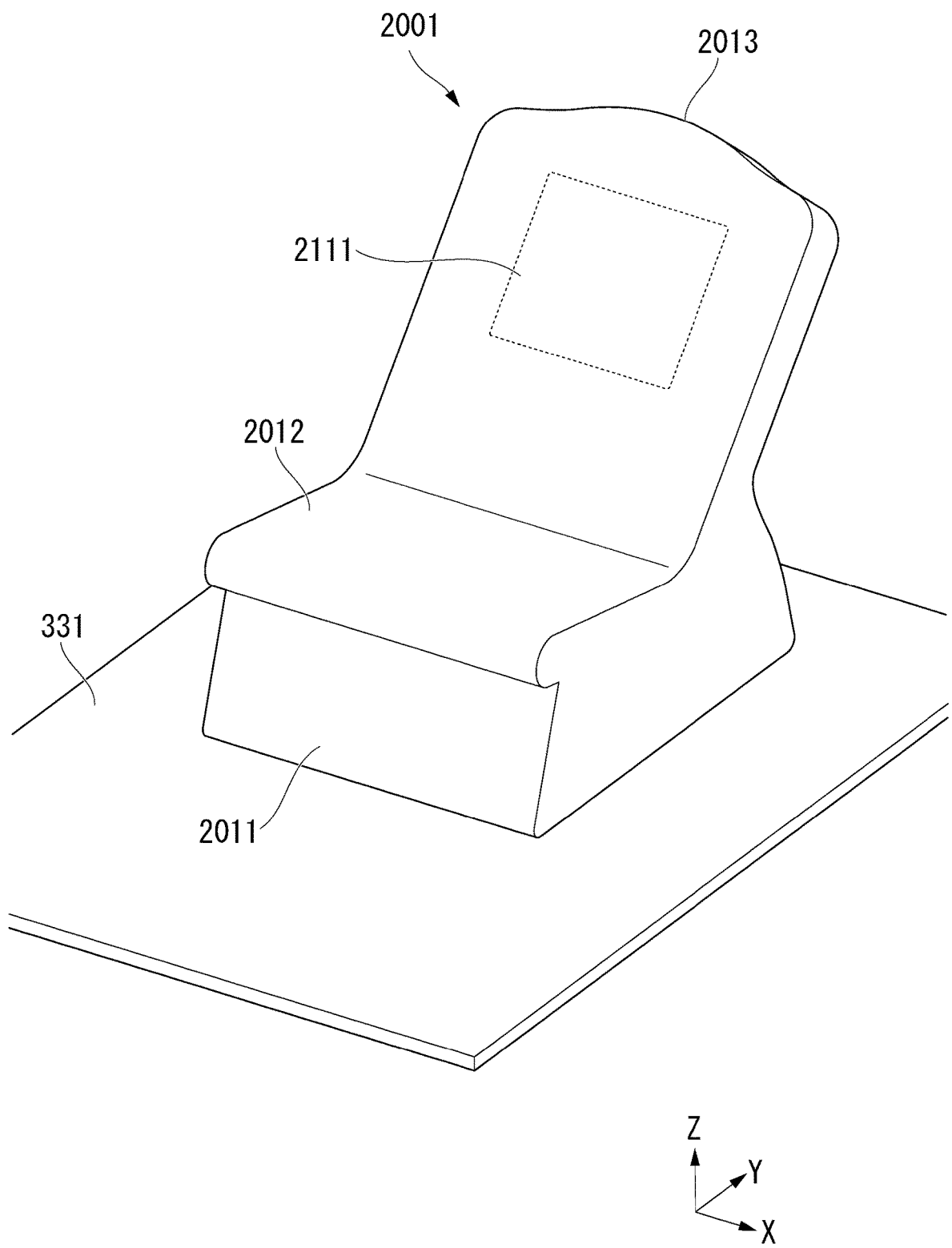
FIG. 19 is a diagram showing an example of a configuration of a chair according to an embodiment (a seventh embodiment).

FIG. 19 is a diagram showing an example of a configuration of a chair 2001 according to an embodiment (a seventh embodiment).

Figure 20:
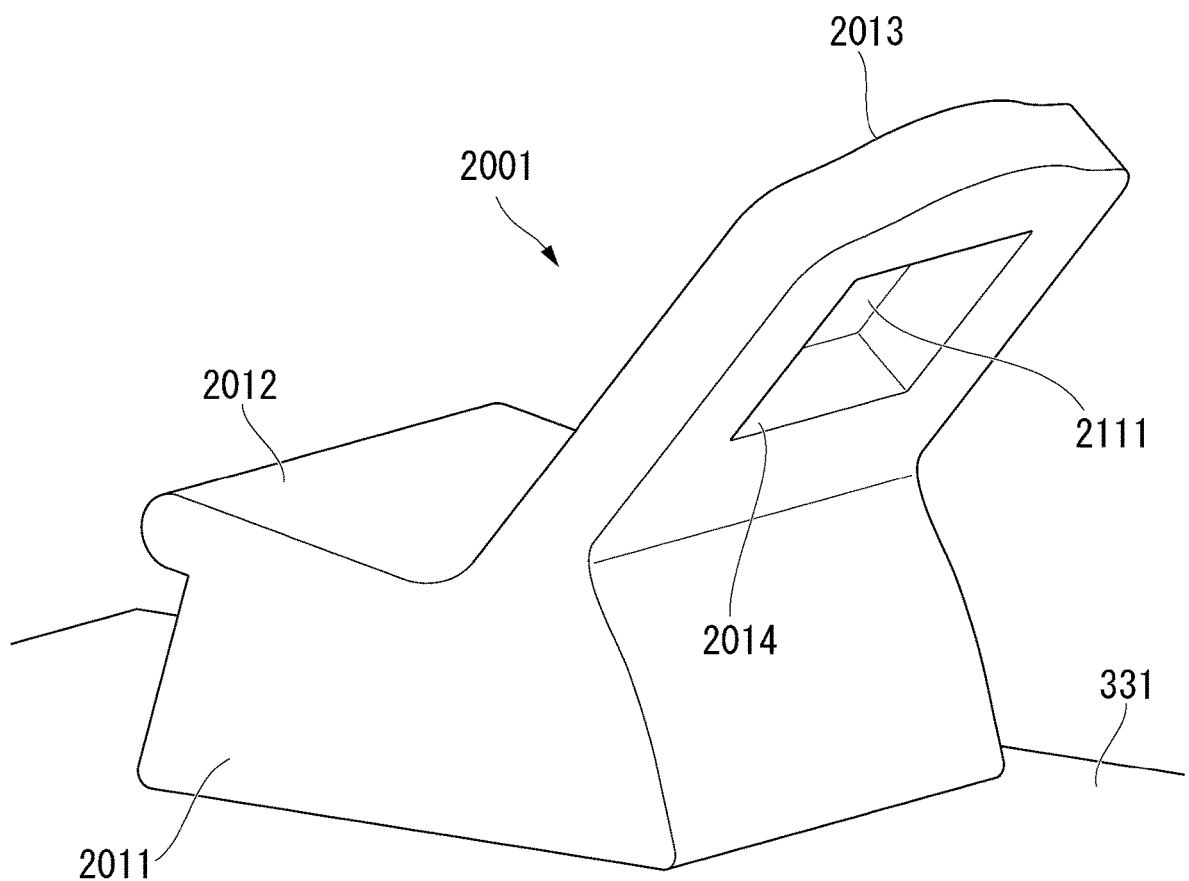
FIG. 20 is a diagram showing an example of a state of a chair viewed from below the back surface according to the embodiment (the seventh embodiment).

FIG. 20 is a diagram showing an example of a state in which the chair 2001 is viewed from below the back surface according to the embodiment (the seventh embodiment).

For convenience of description, an XYZ Cartesian coordinate system, which is a three-dimensional Cartesian coordinate system, is shown in FIGS. 19 and 20.

Also, in FIGS. 19 and 20, a board 331 similar to that shown in FIG. 4 is shown.
<Chair>

The chair 2001 includes a leg portion 2011, a seat surface portion 2012, and a backrest portion 2013.

The backrest portion 2013 has a recess 2014.

The present embodiment is schematically different from the chair 11 shown in FIG. 1 or the chair 311 shown in FIG. 4 in that the recess 2014 has a non-penetration configuration, and others are similar.

In the present embodiment, the recess 2014 is open on the back side of the backrest portion 2013 and is blocked on the upper surface side of the backrest portion 2013.

The recess 2014 has a cover portion 2111 on the upper surface side of the backrest portion 2013. The cover portion 2111 blocks the upper surface side of the backrest portion 2013.

Here, the cover portion 2111, for example, may be integrated with the backrest portion 2013 of the chair 2001 or may be separate from the backrest portion 2013 of the chair 2001.

Also, the cover portion 2111, for example, may be provided fixedly on the chair 2001 or may have a configuration capable of being detached from the chair 2001.

When the cover portion 2111 is detachable from the chair 2001, it is possible to selectively use a state in which one surface of the recess 2014 is covered with the cover portion 2111 and a state in which the recess 2014 is penetrated.

Although the range of the cover portion 2111 is shown for the convenience of description in the example of FIG. 19, for example, the range of the cover portion 2111 may be visually ascertained from above the chair 2001, or may not be visually ascertained from above the chair 2001.

The chair 2001 as shown in FIGS. 19 and 20 may be used in place of the chair in any embodiment.

That is, the recess of the backrest portion of the chair may not necessarily be penetrated.

As described above, in the biological signal measurement device according to the present embodiment, effects similar to those of the above embodiment can be obtained even if the chair 2001 having the recess 2014, which is not penetrated, is used.

Eighth Embodiment

[Modified Example of Placement Portion]

Although a chair is used as a placement portion on which a test subject (for example, a subject) is placed in the above embodiment, other configurations may be used as the placement portion.

For example, as the placement portion, a bed having a surface (for example, a placement surface that is an upper surface) on which the test subject (for example, the subject) can sleep may be used.

In a bed, for example, the subject is placed in a lying position. Examples of the lying position include a supine position (supine), a prone position (face down), and a lateral recumbent position (sideways).

As described above, in the biological signal measurement device according to the present embodiment, effects similar to those of the above embodiment can be obtained even if a placement portion such as a bed is used.

Ninth Embodiment

[Modified Example of Hole Cover]

A modified example of the hole cover 611 shown in FIGS. 10 to 14 will be described with reference to FIGS. 21 and 22.

Figure 21:
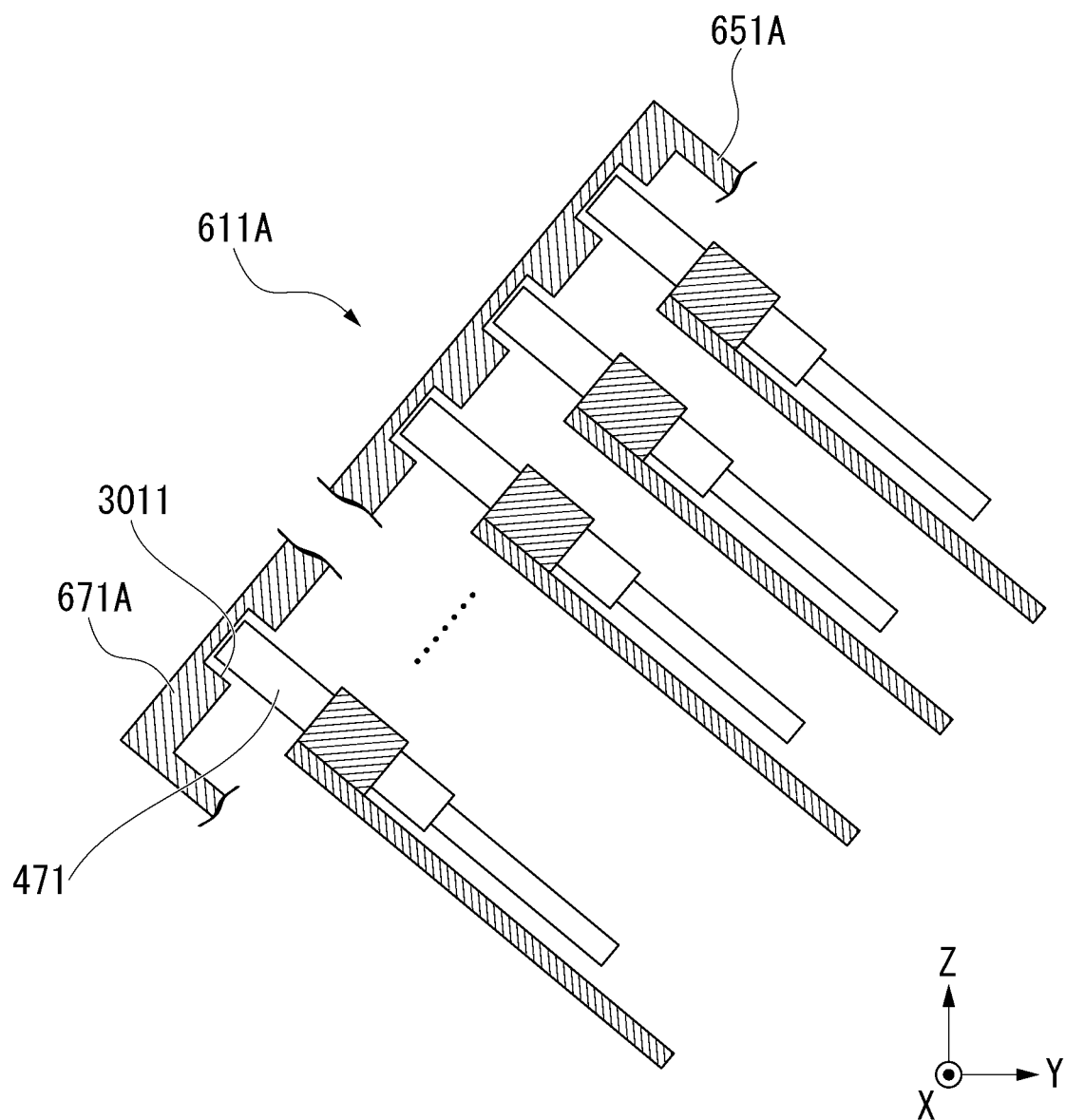
FIG. 21 is a diagram showing an example of a state of a cross-section of a part of a hole cover viewed from a side surface according to an embodiment (a ninth embodiment).

FIG. 21 is a diagram showing an example of a state of a cross-section of a part of a hole cover 611A according to an embodiment (a ninth embodiment) viewed from a side surface.

Figure 22:
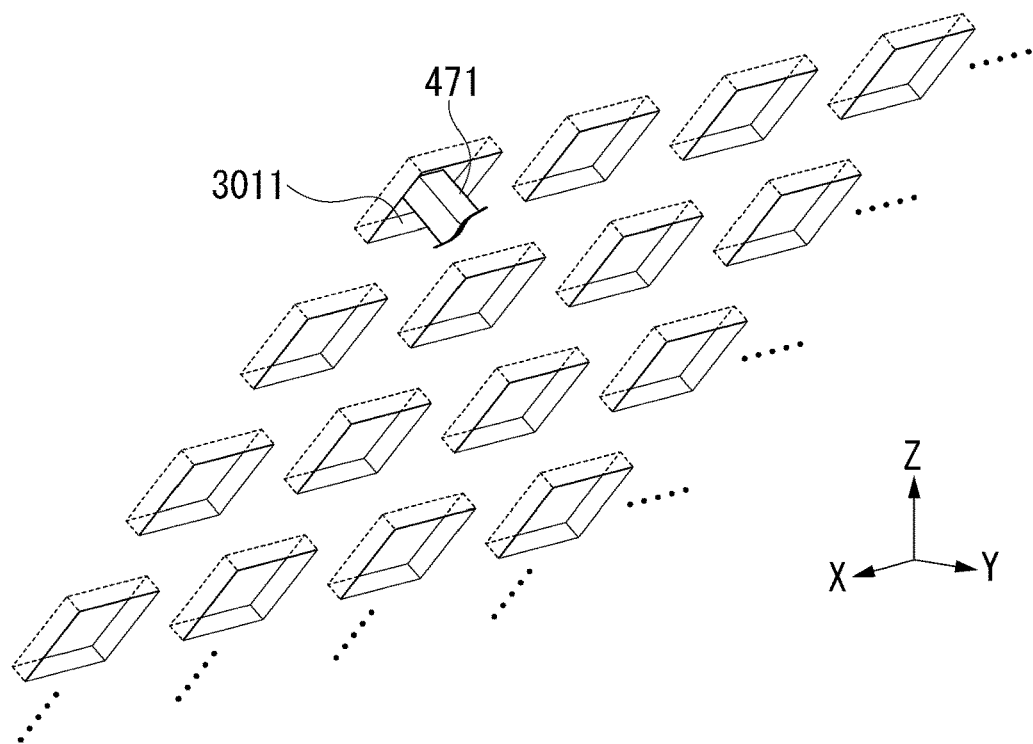
FIG. 22 is a diagram showing an example of a state of a part of the hole cover obliquely viewed from below a back surface according to the embodiment (the ninth embodiment).

FIG. 22 is a diagram showing an example of a state of the part of the hole cover 611A obliquely viewed from below a back surface according to the embodiment (the ninth embodiment).

For convenience of description, an XYZ Cartesian coordinate system similar to those of FIGS. 10 to 14 is shown in FIGS. 21 and 22.

Here, the configuration of the hole cover 611A according to the modified example is different from the configuration of the hole cover 611 shown in FIGS. 10 to 14 in that a configuration near the upper surface portion 671A of the hole cover 611A is different, and the configuration of other portions is similar.

Thus, in the example of FIG. 21, an example of a configuration near the upper surface portion 671A is shown for the hole cover 611A and illustrations of other portions are omitted. The configuration of the other portions is similar to the configuration of the hole cover 611 shown in FIGS. 10 to 14. In addition, in the present embodiment, as in FIGS. 10 to 14, the upper surface portion 671A is a part of a frame portion 651A.

Also, in the example of FIG. 21, only a plurality of measurement sensors 471 are shown as a configuration on the measurement sensor side, and illustrations of other portions are omitted. The configuration of the other portions is similar to those in FIGS. 10 to 14.

In the hole cover 611A, the upper surface portion 671A has a predetermined thickness in a direction perpendicular to the upper surface (a direction from the upper surface to the back surface in the present embodiment) and a recess (a measurement-sensor-specific recess) is provided in a portion corresponding to each measurement sensor 471 in the thickness.

Although such recesses equal in number to a plurality of measurement sensors 471 are provided in the example of FIG. 21, only one recess 3011 is denoted by a reference sign for simplicity of illustration. Also, in the example of FIG. 21, only one measurement sensor 471 corresponding to the recess 3011 is denoted by a reference sign.

Here, each recess has, for example, a similar configuration (for example, a shape or the like).

The recess 3011 has a hole portion from the back surface side to the upper surface side of the upper surface portion 671A having a thickness. The hole portion is not penetrated on the upper surface side.

The recess 3011 houses a tip portion of the measurement sensor 471 (here, a tip portion on the upper surface side) arranged at a position corresponding to the recess 3011, and has a shape that does not come into contact with the tip portion. Although the tip portion may be accommodated to a depth of about 90% of the depth of the recess 3011 as an example, other forms may be used.

In the example of FIG. 22, an arrangement relationship between the measurement sensor 471 and the recess 3011 is shown, and only the tip portion of one measurement sensor 471 is illustrated for simplicity of illustration. Also, only one measurement sensor 471 and one recess 3011 are denoted by reference signs. An arrangement relationship between them is similar to that in the case of FIG. 21.

As described above, in the biological signal measurement device according to the present embodiment, the recess 3011 accommodating the tip portion among thick portions provided in the upper surface portion 671A of the hole cover 611A is provided without coming into contact with the tip portion of each measurement sensor 471 at a position corresponding to each measurement sensor 471.

Therefore, in the biological signal measurement device according to the present embodiment, when the hole cover 611A is thick, as compared with the case where the recess 3011 is not provided in a portion of the thickness, it is possible to make the measurement sensor 471 closer to the subject (the back of the subject sitting in the chair 311 in the present embodiment) by maintaining an arrangement in which the measurement sensor 471 does not come into contact with the hole cover 611A and it is possible to measure a target signal with higher accuracy.

Here, various forms may be used as the shape of the recess 3011.

Although an example of a configuration in which one recess 3011 is provided for each measurement sensor 471 has been described in the present embodiment, a configuration in which one recess is formed for each assembly of two or more measurement sensors (here, a number of measurement sensors less in number than a total number of measurement sensors) may be adopted as another example.

In addition, the recess 3011 may be referred to as, for example, a depression, a hole portion, a counterbore, or the like.

Tenth Embodiment

[Biological Signal Measurement Device Having Anti-Vibration Portion]

Although the anti-vibration portion has also been described in the above embodiment, an example of a configuration focusing on the anti-vibration portion is shown in the present embodiment.

Referring to FIGS. 23 to 26, an example of a biological signal measurement device having an anti-vibration portion is shown.

Here, a case where the anti-vibration portion is applied to the chair 311 and the sensor holder 321 shown in FIGS. 4 to 9 is shown in the examples of FIGS. 23 to 26.

For convenience of description, XYZ Cartesian coordinate systems similar to those shown in FIGS. 4 to 9 are shown in FIGS. 23 to 26.

In addition, in the example of FIGS. 23 to 26, for simplicity of the illustration, the illustration of reference signs of detailed components for the chair 311 and the sensor holder 321 is omitted.

First Example

Figure 23:
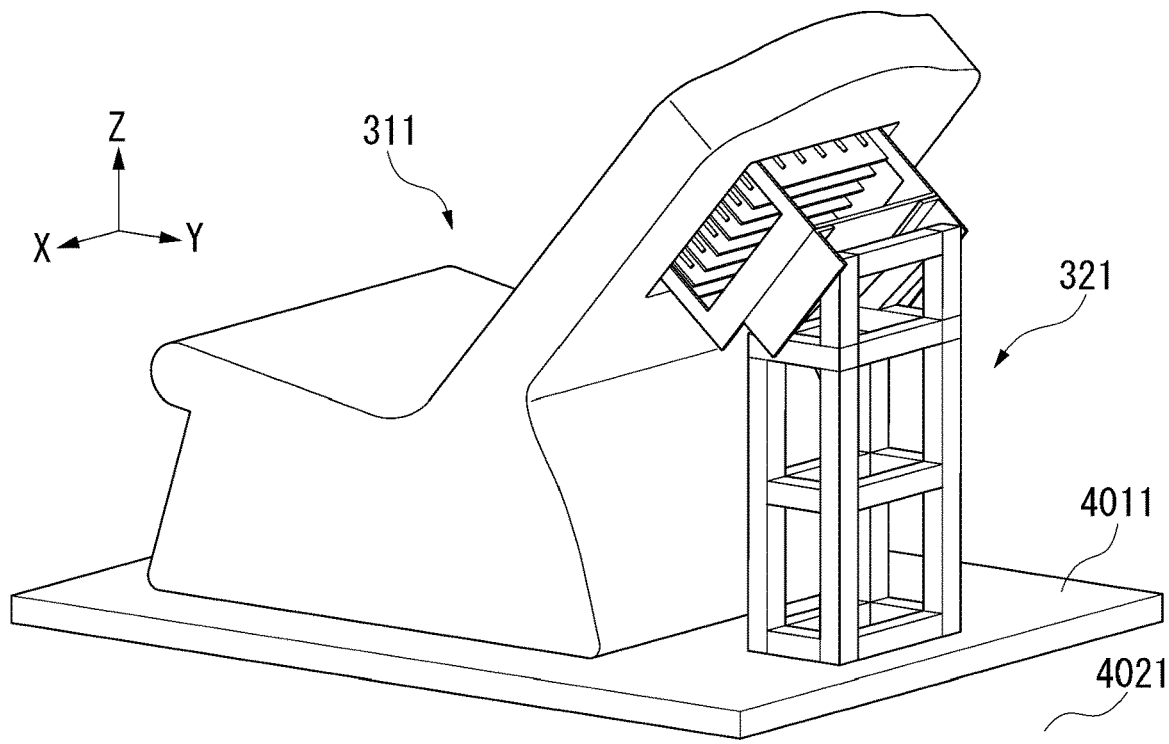
FIG. 23 is a diagram showing a first example of a configuration of a biological signal measurement device having an anti-vibration portion according to an embodiment (a tenth embodiment).

FIG. 23 is a diagram showing a first example of a configuration of a biological signal measurement device having an anti-vibration portion 4011 according to the embodiment (the tenth embodiment).

In the present example, the biological signal measurement device includes a chair 311, a sensor holder 321, and the anti-vibration portion 4011.

The anti-vibration portion 4011 is arranged below the chair 311 and the sensor holder 321. The anti-vibration portion 4011 has, for example, a shape of a flat plate, and the chair 311 and the sensor holder 321 are placed on the surface of the flat plate.

The anti-vibration portion 4011 has a function of preventing vibration, and may be made of, for example, a vibration isolation mat.

One surface (lower surface) of the flat plate of the anti-vibration portion 4011 is placed on a planar floor 4021.

The chair 311 and the sensor holder 321 are placed on the other surface (upper surface) of the flat plate of the anti-vibration portion 4011.

In addition, the floor 4021, for example, may not be included as a component of the biological signal measurement device.

Thus, in the biological signal measurement device according to the first example, a common anti-vibration portion 4011 (an integrated anti-vibration portion 4011) is provided on the lower side of the chair 311 and the sensor holder 321.

Therefore, in the biological signal measurement device according to the first example, for example, the vibration transmitted to the measurement sensor via the floor 4021 is reduced and the superposition of a vibration component on the measured signal can be prevented. Here, vibrations include, for example, the minute shaking of the building itself, the natural vibration of the chair 311 or the sensor holder 321, the vibration derived from the body motion of the subject, and the like.

Also, in the biological signal measurement device according to the first example, for example, the vibration transmitted to the chair 311 and the subject via the floor 4021 is reduced, thereby improving the accuracy of the measurement.

Second Example

Figure 24:
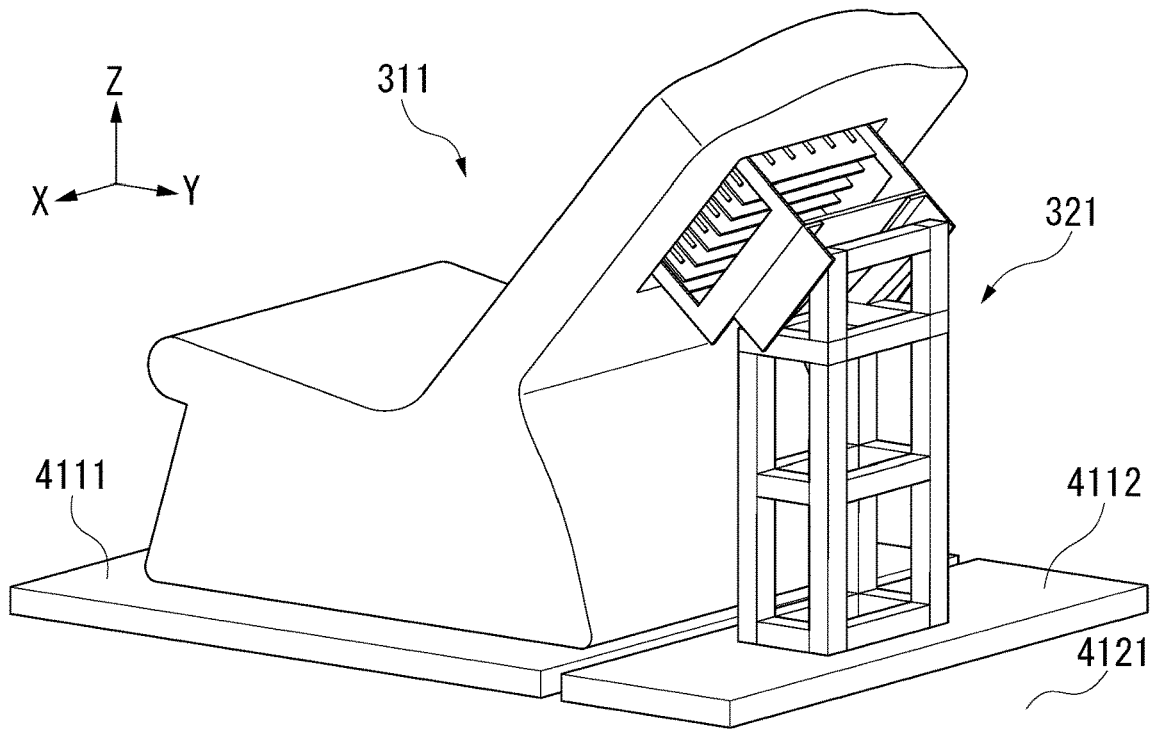
FIG. 24 is a diagram showing a second example of the configuration of the biological signal measurement device having the anti-vibration portion according to the embodiment (the tenth embodiment).

FIG. 24 is a diagram showing a second example of a configuration of a biological signal measurement device having anti-vibration portions 4111 and 4112 according to the embodiment (the tenth embodiment).

In the present example, the biological signal measurement device includes a chair 311, a sensor holder 321, and two anti-vibration portions 4111 to 4112.

The two anti-vibration portions 4111 to 4112 are arranged on the upper side of a floor 4121.

Here, the configuration of the biological signal measurement device according to the second example is different from the configuration of the biological signal measurement device according to the first example in that the anti-vibration portion 4111 arranged on the lower side of the chair 311 and the anti-vibration portion 4112 arranged on the lower side of the sensor holder 321 are provided as separate components, and others are similar.

Thus, in the biological signal measurement device according to the second example, the anti-vibration portion 4111 is provided on the lower side of the chair 311, and the anti-vibration portion 4112 is provided on the lower side of the sensor holder 321.

Therefore, in the biological signal measurement device according to the second example, for example, the vibration transmitted to the measurement sensor via the floor 4121 is reduced and the superposition of the vibration component on the measured signal can be prevented.

Also, in the biological signal measurement device according to the second example, for example, the vibration transmitted to the chair 311 and the subject via the floor 4121 is reduced, thereby improving the accuracy of the measurement.

Third Example

Figure 25:
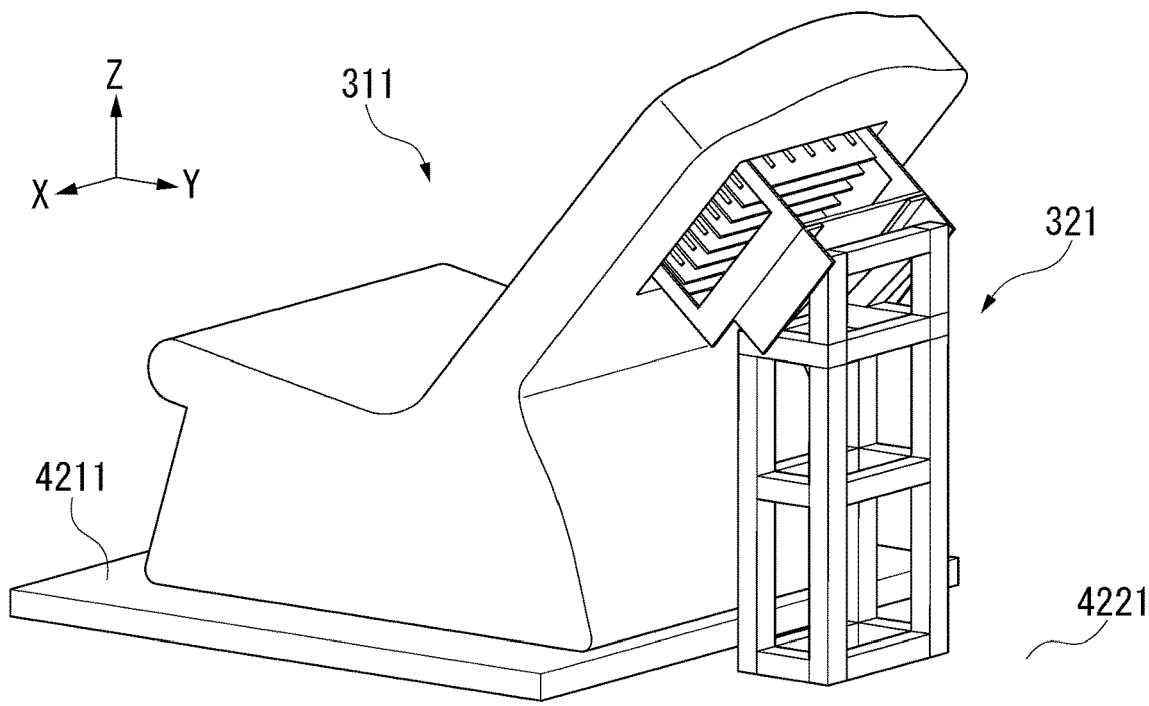
FIG. 25 is a diagram showing a third example of the configuration of the biological signal measurement device having the anti-vibration portion according to the embodiment (the tenth embodiment).

FIG. 25 is a diagram showing a third example of a configuration of a biological signal measurement device having an anti-vibration portion 4211 according to the embodiment (the tenth embodiment).

In the present example, the biological signal measurement device includes a chair 311, a sensor holder 321, and the anti-vibration portion 4211.

The anti-vibration portion 4211 is arranged on the upper side of a floor 4221.

Here, the configuration of the biological signal measurement device according to the third example is schematically different from the configuration of the biological signal measurement device according to the second example in that the anti-vibration portion 4211 is arranged on the lower side of a chair 311 but no anti-vibration portion is arranged on a lower side of the sensor holder 321, and others are similar. In addition, for example, heights of one or both of the chair 311 and the sensor holder 321 may be arbitrarily adjusted in accordance with a thickness of the anti-vibration portion 4211 in the upward/downward direction.

Thus, in the biological signal measurement device according to the third example, the anti-vibration portion 4211 is provided on the lower side of the chair 311.

Therefore, in the biological signal measurement device according to the third example, for example, vibration transmitted to the chair 311 and the subject via the floor 4221 is reduced, thereby improving the accuracy of the measurement.

Fourth Example

Figure 26:
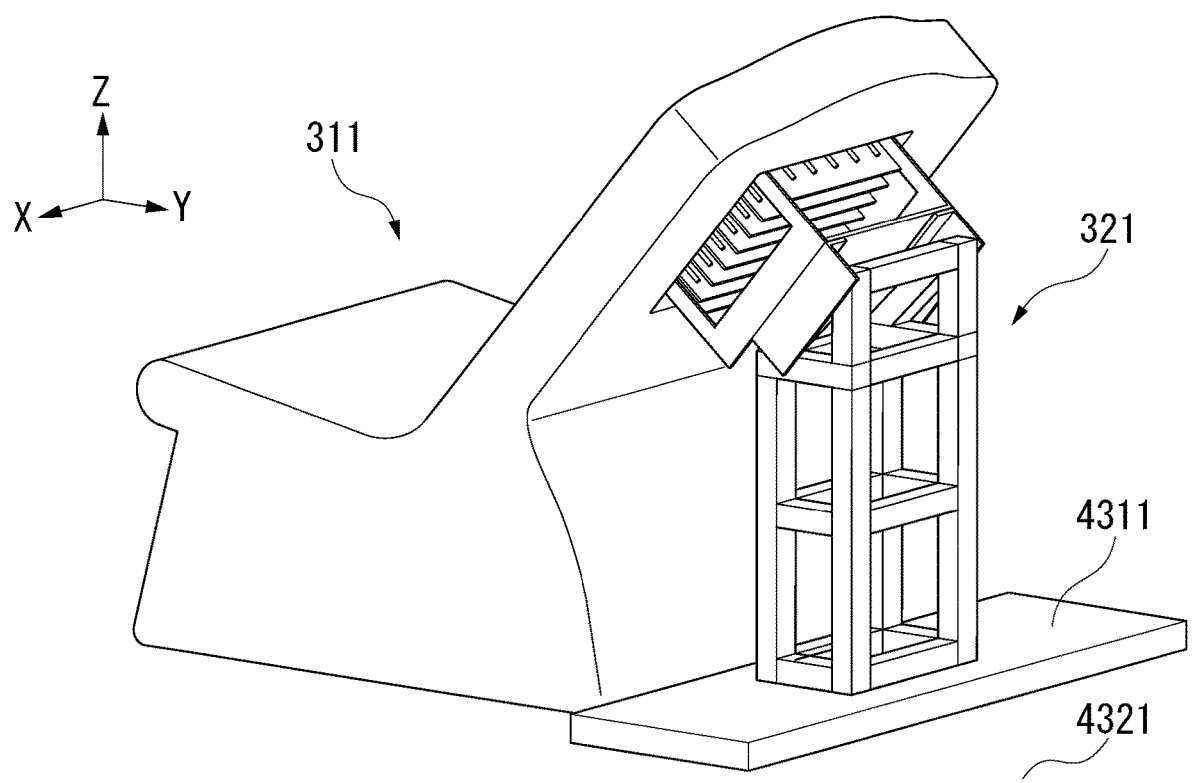
FIG. 26 is a diagram showing a fourth example of the configuration of the biological signal measurement device having the anti-vibration portion according to the embodiment (the tenth embodiment).

FIG. 26 is a diagram showing a fourth example of a configuration of a biological signal measurement device having an anti-vibration portion 4311 according to the embodiment (the tenth embodiment).

In the present example, the biological signal measurement device includes a chair 311, a sensor holder 321, and the anti-vibration portion 4311.

The anti-vibration portion 4311 is arranged on an upper side of a floor 4321.

Here, the configuration of the biological signal measurement device according to the fourth example is schematically different from the configuration of the biological signal measurement device according to the second example in that no anti-vibration portion is arranged on the lower side of the chair 311 but the anti-vibration portion 4311 is arranged on the lower side of the sensor holder 321, and others are similar. In addition, for example, heights of one or both of the chair 311 and the sensor holder 321 may be arbitrarily adjusted in accordance with the thickness of the anti-vibration portion 4311 in the upward/downward direction.

Thus, in the biological signal measurement device according to the fourth example, the anti-vibration portion 4311 is provided on the lower side of the sensor holder 321.

Therefore, in the biological signal measurement device according to the fourth case, for example, the vibration transmitted to the measurement sensor via the floor 4321 is reduced, and the superposition of the vibration component on the measured signal can be prevented.

Regarding First to Fourth Examples

In addition, examples of the configuration of the anti-vibration portion according to the first to fourth examples are shown and various other configurations of the anti-vibration portion may be used.

Although the case where the anti-vibration portion is applied to the chair 311 and the sensor holder 321 shown in FIGS. 4 to 9 has been described in the first to fourth examples, a configuration in which an anti-vibration portion is applied to the chair and the sensor holder according to other configuration examples may be used.

Also, various forms may be used as the material of the anti-vibration portion and the like.

Regarding Above Embodiments

Although embodiments of the present disclosure have been described in detail above with reference to the drawings, specific configurations are not limited to the embodiments and other designs and the like may also be included without departing from the scope of the present disclosure.

APPENDIXES

Hereinafter, configuration examples are shown.

Configuration Example 1

A biological signal measurement device including:
a placement portion on which a test subject is placed;
one or more measurement sensors configured to measure a biological signal regarding the test subject; and
a sensor holder configured to hold the measurement sensors,
wherein the placement portion has a recess,
wherein at least a part of the measurement sensor is arranged inside of the recess of the placement portion, and
wherein the sensor holder and the measurement sensors are arranged to be physically separated from the placement portion without coming into contact with the placement portion.

Configuration Example 2

The biological signal measurement device according to [Configuration example 1], including an anti-vibration portion arranged between at least one of the placement portion and the sensor holder and a floor.

Configuration Example 3

The biological signal measurement device according to [Configuration example 1] or [Configuration example 2], including a sensor housing portion configured to house the measurement sensors,
wherein the sensor housing portion has a structure included in the sensor holder or a structure capable of being attached to the sensor holder separately from the sensor holder.

Configuration Example 4

The biological signal measurement device according to [Configuration example 3], wherein the sensor housing portion has a structure in which a plurality of measurement sensors are arranged in an array shape.

Configuration Example 5

The biological signal measurement device according to any one of [Configuration examples 1 to 4], including a hole cover,
wherein the recess of the placement portion is a through-hole,
wherein the hole cover is attached to the through-hole, and
wherein the hole cover is arranged to be physically separated from the sensor holder and the measurement sensor without coming into contact with the sensor holder and the measurement sensor.

Configuration Example 6

The biological signal measurement device according to [Configuration example 5], including a recess (a measurement-sensor-specific recess) provided on the side of the measurement sensor of the hole cover and at a part where the measurement sensor is arranged.

Configuration Example 7

The biological signal measurement device according to [Configuration example 5] or [Configuration example 6],
wherein the measurement sensor is a magnetic sensor, and
wherein the hole cover is made of a non-magnetic body.

Configuration Example 8

The biological signal measurement device according to any one of [Configuration examples 1 to 7], including a placement portion adjustment portion configured to adjust at least one of a position and an angle of a part of the placement portion.

Configuration Example 9

The biological signal measurement device according to any one of [Configuration examples 1 to 8], including a measurement sensor adjustment portion provided on the sensor holder and configured to directly or indirectly adjust at least one of a position and an angle of the measurement sensor.

Configuration Example 10

The biological signal measurement device according to any one of [Configuration examples 1 to 9], including:
one or more reference sensors configured to measure environmental noise; and
a reference sensor holder configured to hold the reference sensors,
wherein the reference sensor holder and the reference sensors are arranged to be physically separated from the placement portion without coming into contact with the placement portion.

Configuration Example 11

The biological signal measurement device according to any one of [Configuration examples 1 to 10],
wherein the measurement sensor is a magnetic sensor, and
wherein the placement portion includes a non-magnetic body.

Configuration Example 12

The biological signal measurement device according to any one of [Configuration examples 1 to 11],
wherein the placement portion is a chair, and
wherein the recess is formed in a backrest portion of the chair.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES

1, 301, 301a, 301b, 801, 1001 Biological signal measurement device
11, 311, 311a, 2001 Chair
21, 321, 321b, 321c Sensor holder
31, 331 Board
111, 411, 911A, 2011 Leg portion
112, 412, 2012 Seat surface portion
113, 413, 2013 Backrest portion
114, 414, 2014, 3011 Recess
151 Tripod portion
152, 912A Shaft portion
153 Connection portion
161 Attachment portion
171, 471 Measurement sensor
211 Subject
451 Base portion
452 Support portion
461 Sensor housing portion
511 Hole portion
611, 611A Hole cover
651, 651A Frame portion
661 to 664 L-shaped portion
671, 671A Upper surface portion
711 Chair adjustment portion
751 Measurement sensor adjustment portion
821A, 821B, 1111A, 1111B Reference sensor holder
911A Leg portion
913A Reference sensor housing portion
921A, 921B, 1121A, 1121B Reference sensor
2111 Cover portion
4011, 4111, 4112, 4211, 4311 Anti-vibration portion
4021, 4121, 4221, 4321 Floor

What is claimed is:

1. A biological signal measurement device comprising:
a placement portion on which a test subject is placed;
one or more measurement sensors configured to measure a biological signal regarding the test subject;
a sensor holder configured to hold the measurement sensors;
a hole cover; and
a measurement-sensor-specific recess provided on a side of the measurement sensor of the hole cover and at a position where the measurement sensor is arranged,
wherein each of the measurement-sensor-specific recess is provided for each of the measurement sensor,
wherein the placement portion has a recess,
wherein at least a tip portion of the measurement sensor is arranged inside of the recess of the placement portion such that the measurement sensor does not contact with the test subject,
wherein the sensor holder and the measurement sensors are arranged to be physically separated from the placement portion without coming into contact with the placement portion when the biological signal is measured,
wherein the recess of the placement portion is a through-hole,
wherein the hole cover is attached to the through-hole,
wherein the hole cover is arranged to be physically separated from the sensor holder and the measurement sensor without coming into contact with the sensor holder and the measurement sensor, and
wherein the hole cover is provided to cover the recess and also becomes a support portion to support the test subject while the test subject is placed on the placement portion.

2. The biological signal measurement device according to claim 1, comprising an anti-vibration portion arranged between at least one of the placement portion and the sensor holder and a floor.

3. The biological signal measurement device according to claim 1, comprising a sensor housing portion configured to house the measurement sensors,
wherein the sensor housing portion has a structure included in the sensor holder or a structure capable of being attached to the sensor holder separately from the sensor holder.

4. The biological signal measurement device according to claim 3, wherein the sensor housing portion has a structure in which a plurality of measurement sensors are arranged in an array shape.

5. The biological signal measurement device according to claim 1,
wherein the measurement sensor is a magnetic sensor, and
wherein the hole cover is made of a non-magnetic body.

6. The biological signal measurement device according to claim 1, comprising a placement portion adjustment portion configured to adjust at least one of a position and an angle of a part of the placement portion.

7. The biological signal measurement device according to claim 1, comprising a measurement sensor adjustment portion provided on the sensor holder and configured to directly or indirectly adjust at least one of a position and an angle of the measurement sensor.

8. The biological signal measurement device according to claim 1, comprising:
one or more reference sensors configured to measure environmental noise; and
a reference sensor holder configured to hold the reference sensors,
wherein the reference sensor holder and the reference sensors are arranged to be physically separated from the placement portion without coming into contact with the placement portion.

9. The biological signal measurement device according to claim 1,
wherein the measurement sensor is a magnetic sensor, and
wherein the placement portion includes a non-magnetic body.

10. The biological signal measurement device according to claim 1,
wherein the placement portion is a chair, and
wherein the recess is formed in a backrest portion of the chair.

* * * * *